(12) United States Patent
Donaldson et al.

(10) Patent No.: US 12,059,141 B2
(45) Date of Patent: *Aug. 13, 2024

(54) SYSTEMS AND METHODS RELATING TO MEDICAL APPLICATIONS OF SYNTHETIC POLYMER FORMULATIONS

(71) Applicant: Critical Innovations, LLC, Inglewood, CA (US)

(72) Inventors: Ross I. Donaldson, Inglewood, CA (US); Timothy Fisher, Inglewood, CA (US); Oliver Buchanan, Inglewood, CA (US); Jon Armstrong, Inglewood, CA (US); John Cambridge, Inglewood, CA (US)

(73) Assignee: Critical Innovations, LLC, Inglewood, CA (US)

( * ) Notice: Subject to any disclaimer, the term of this patent is extended or adjusted under 35 U.S.C. 154(b) by 190 days.

This patent is subject to a terminal disclaimer.

(21) Appl. No.: 17/549,432

(22) Filed: Dec. 13, 2021

(65) Prior Publication Data

US 2022/0104798 A1 Apr. 7, 2022

Related U.S. Application Data

(63) Continuation of application No. 16/354,418, filed on Mar. 15, 2019, now Pat. No. 11,207,060.

(Continued)

(51) Int. Cl.
*A61B 17/00* (2006.01)
*A61L 24/00* (2006.01)
*A61L 24/04* (2006.01)

(52) U.S. Cl.
CPC ...... *A61B 17/0057* (2013.01); *A61L 24/0026* (2013.01); *A61L 24/0042* (2013.01);
(Continued)

(58) Field of Classification Search
CPC ............... A61B 17/00; A61B 17/0057; A61B 17/00491; A61B 2017/00778; A61L 24/0042; A61L 24/0026
See application file for complete search history.

(56) References Cited

U.S. PATENT DOCUMENTS

| 4,474,752 A | 10/1984 | Haslam et al. |
| 6,187,290 B1 | 2/2001 | Gilchrist et al. |

(Continued)

FOREIGN PATENT DOCUMENTS

| WO | 2009090558 A2 | 7/2009 |
| WO | 2022/226300 A1 | 10/2022 |

OTHER PUBLICATIONS

Zhao Y et al: "Engineering novel topical foams using hydrofluroalkane emulsions stabilised with pluronic surfactants", European Journal of Pharmaceutical Sciences, Elsevier, Amsterdam, NL, vol. 37, No. 3-4 Jun. 28, 2009 (Jun. 28, 2009), pp. 370-377.

(Continued)

*Primary Examiner* — Vi X Nguyen
(74) *Attorney, Agent, or Firm* — Merchant & Gould P.C.

(57) ABSTRACT

Systems, methods and compositions relating to delivering synthetic polymer formulations to the body are described, which can be used by a range of medical personnel including those with minimal experience and training. Under some embodiments, the present invention relates to systems and devices for delivering polymer formulations to a body cavity (e.g. peritoneal cavity) to reduce or stop bleeding. Under some embodiments, an initial percutaneous access pathway is first formed using a delivery device with a probe and needle mechanism that automatically stops the advance of the device upon insertion into a body cavity or space, thus minimizing user error and improving patient safety. The hollow probe then allows transmission of polymer, mixed with gas and/or additional substances, from a holding cham- (Continued)

ber or canister to flow through the device and hollow probe into the patient's anatomic cavity or space of interest, stopping expansion when the device senses the appropriate pressure. Once reaching the body cavity, the polymer formulation functions to reduce and/or stop bleeding.

19 Claims, 17 Drawing Sheets

Related U.S. Application Data

(60) Provisional application No. 62/643,846, filed on Mar. 16, 2018.

(52) U.S. Cl.
CPC ... *A61L 24/046* (2013.01); *A61B 2017/00495* (2013.01); *A61B 2017/00522* (2013.01); *A61B 2017/00778* (2013.01); *A61B 2017/00818* (2013.01); *A61B 2017/00884* (2013.01); *A61B 2017/00889* (2013.01); *A61B 2017/00893* (2013.01); *A61B 2017/00898* (2013.01); *A61L 2300/404* (2013.01); *A61L 2300/418* (2013.01); *A61L 2430/36* (2013.01)

(56) References Cited

U.S. PATENT DOCUMENTS

| | | | |
|---|---|---|---|
| 6,316,011 B1 | 11/2001 | Ron et al. | |
| 7,229,433 B2 * | 6/2007 | Mullen | A61B 17/3415 604/164.04 |
| 8,062,282 B2 | 11/2011 | Kolb | |
| 8,198,365 B2 | 6/2012 | Ingenito | |
| 8,497,408 B2 * | 7/2013 | Wnek | A61B 17/122 602/56 |
| 8,668,899 B2 | 3/2014 | Dowling et al. | |
| 8,828,050 B2 | 9/2014 | Gregory et al. | |
| 9,283,278 B2 | 3/2016 | Rodeheaver et al. | |
| 9,616,088 B2 | 4/2017 | Diehn et al. | |
| 9,884,136 B2 | 2/2018 | Rodeheaver et al. | |
| 10,111,834 B2 | 10/2018 | Laub | |
| 10,456,416 B2 | 10/2019 | Koller et al. | |
| 10,857,100 B2 | 12/2020 | Laub | |
| 2002/0122771 A1 | 9/2002 | Holland et al. | |
| 2003/0095945 A1 | 5/2003 | Levey et al. | |
| 2003/0203044 A1 | 10/2003 | Moravec | |
| 2004/0013715 A1 | 1/2004 | Winek et al. | |
| 2005/0008610 A1 | 1/2005 | Schwarz et al. | |
| 2005/0064021 A1 | 3/2005 | Rippon et al. | |
| 2005/0147585 A1 | 7/2005 | Schwarz | |
| 2006/0100370 A1 | 5/2006 | Wellisz et al. | |
| 2006/0193899 A1 | 8/2006 | Sawhney | |
| 2007/0191768 A1 | 8/2007 | Kolb | |
| 2008/0031847 A1 | 2/2008 | Cohn et al. | |
| 2008/0181952 A1 | 7/2008 | Vogel | |
| 2008/0208163 A1 | 8/2008 | Wilkie | |
| 2009/0041824 A1 | 2/2009 | Zugates et al. | |
| 2009/0254195 A1 * | 10/2009 | Khairkhahan | A61B 17/12122 623/23.67 |
| 2009/0286886 A1 | 11/2009 | Fisher et al. | |
| 2011/0087207 A1 | 4/2011 | Vogel et al. | |
| 2011/0202016 A1 | 8/2011 | Zugates et al. | |
| 2011/0294760 A1 | 12/2011 | Bahulekar et al. | |
| 2012/0107439 A1 | 5/2012 | Sharma et al. | |
| 2012/0265287 A1 | 10/2012 | Sharma et al. | |
| 2013/0110066 A1 | 5/2013 | Sharma et al. | |
| 2013/0158589 A1 | 6/2013 | Cohn et al. | |
| 2013/0317418 A1 | 11/2013 | Freyman et al. | |
| 2014/0271531 A1 | 9/2014 | Freyman et al. | |
| 2014/0271533 A1 | 9/2014 | Freyman et al. | |
| 2014/0316012 A1 | 10/2014 | Freyman et al. | |
| 2016/0256170 A1 | 9/2016 | Busold et al. | |
| 2016/0271293 A1 | 9/2016 | Zugates et al. | |
| 2017/0216480 A1 | 8/2017 | Rodeheaver et al. | |
| 2018/0169012 A1 | 6/2018 | Laub | |
| 2023/0064184 A1 | 3/2023 | Laub | |

OTHER PUBLICATIONS

European Search Report from EPO regarding Application No. EP 23168595 dated Sep. 20, 2023.
Extended European Search Report from EPO regarding Application No. EP 19163317 dated Aug. 2, 2019.

\* cited by examiner

Figure 15

| Poloxamer | Pluronic® | Average molecular mass (kg/mol) | Mass % of EO (as Oxyethylene) |
|---|---|---|---|
| P188 | F68 | 7680 - 9510 | 81.8 ± 1.9 |
| P237 | F87 | 6840 - 8830 | 72.4 ± 1.9 |
| P338 | F108 | 12700 - 17400 | 83.1 ± 1.7 |
| P407 | F127 | 9840 - 14600 | 73.2 ± 1.7 |

Figure 16

| Polymer Solution | | Gas content | Foam Ratio | | Specific Volume (cm³/g) | | Foam Stability |
|---|---|---|---|---|---|---|---|
| Pluronic | wt% | wt% | Peak | 60 minutes | Peak | 60 minutes | FR 60 / FR Peak |
| F68 | 37.5% | 10.0% | 0.96 | 0.89 | 25.5 | 24.0 | 92% |
| F68 | 41.0% | 10.0% | 0.94 | 0.90 | 21.1 | 21.0 | 97% |
| F68 | 45.0% | 10.0% | 0.94 | 0.92 | 24.2 | 23.5 | 98% |
| F68 | 37.5% | 5.0% | 0.96 | 0.89 | 13.6 | 12.7 | 94% |
| F108 | 37.5% | 2.5% | 0.88 | 0.69 | 4.2 | 3.7 | 78% |
| F108 | 37.5% | 5.0% | 0.92 | 0.79 | 11.1 | 9.9 | 86% |
| F108 | 37.5% | 10.0% | 0.86 | 0.12 | 20.6 | 2.9 | 14% |
| F127 | 25.0% | 5.0% | 0.57 | 0.39 | 7.4 | 5.2 | - |
| F127 | 30.0% | 5.0% | 0.91 | 0.23 | 9.2 | 3.0 | 26% |
| F127 | 34.0% | 5.0% | 0.90 | 0.34 | 10.3 | 4.4 | 38% |
| F127 | 37.5% | 5.0% | 0.44 | 0.30 | 5.4 | 3.6 | - |
| F127 | 30.0% | 10.0% | 0.54 | 0.16 | 11.4 | 3.7 | - |

Figure 17

| Polymer Solution | | Gelation Temp. |
|---|---|---|
| Pluronic | wt% | °C |
| F68 | 37.5% | 36.3 |
| F68 | 41.0% | 30.8 |
| F68 | 45.0% | 24.4 |
| F108 | 37.5% | 7.6 |
| F127 | 25.0% | 17.6 |
| F127 | 30.0% | 13.2 |
| F127 | 34.0% | 9.7 |
| F127 | 37.5% | 6.7 |

US 12,059,141 B2

SYSTEMS AND METHODS RELATING TO MEDICAL APPLICATIONS OF SYNTHETIC POLYMER FORMULATIONS

RELATED APPLICATIONS

The present application is a continuation of U.S. application Ser. No. 16/354,418 filed Mar. 15, 2019, which claims the benefit of U.S. Provisional Application No. 62/643,846 filed Mar. 16, 2018, which are hereby incorporated herein in its entirety by reference.

U.S. patent application Ser. No. 13/961,422, filed Aug. 7, 2013 and entitled Method and Device for Simultaneously Documenting and Treating Tension Pneumothorax and/or Hemothorax and U.S. patent application Ser. No. 14/581,339, filed Dec. 23, 2014 and entitled Percutaneous Channel System and Method, and U.S. patent application Ser. No. 17/961,422, filed Sep. 22, 2017 and titled Percutaneous Access Pathway System, all having at least one of the same inventors, are hereby incorporated by reference herein in their entirety.

FIELD OF THE INVENTION

The present disclosure relates generally to the medical field, and more particularly, to systems and methods relating to the medical applications of synthetic polymer formulations. In one application, the present invention relates to systems and devices for delivering resorbable synthetic polymer formulations to the body.

BACKGROUND OF THE INVENTION

A wide variety of diagnostic and/or therapeutic procedures involve the delivery of synthetic polymers to the body. One objective is to provide hemostasis of bleeding vessels and other organs. This bleeding may be internal or external in nature and from all sites on the body. Another objective is to provide the delivery of pharmaceutical agents (e.g. hemostatic agents, antibiotics, anesthetics). This delivery may be to all sites on the body, internal or external.

A recent review of U.S. battlefield deaths from 2001-2011 demonstrated that around 90% of all injury mortality occurred in the pre-medical treatment facility environment. Of the potentially survivable deaths, the vast majority were due to hemorrhage (90%), with the bleeding coming in order of frequency from the abdominopelvic, thoracic, junctional, extremity areas.

Internal bleeding (e.g. abdominopelvic and thoracic) is particularly difficulty to stop without highly specialized care facilities. Civilian studies have found that for major traumatic injuries in the abdomen, the probability of death increases approximately 1% for each 3-minute delay to surgery. American military experts have declared that the inability to stop intra-abdominal bleeding quickly in the field "signifies a clear and persistent gap in medical treatment capability that has been present for the entire history of warfare and well documented for nearly a century."

The gold standard for severe traumatic intra-abdominal bleeding is emergent laparotomy, which requires the lengthy training and perishable skills of a trauma surgeon, as well as a sterile operating room. As the majority of the U.S. combat deaths are in the pre-medical treatment facility environment, reducing them requires a technology that personnel with limited training can deploy rapidly, in the out-of-hospital or in-hospital environments.

The literature discloses various known systems and methods related to delivering hemorrhage control to the body.

For example, U.S. Pat. No. 8,828,050 B2 to Gregory et al. describes an applicator for delivering a plurality of sponges capable of expanding upon contact with a liquid to a body cavity. Related product information from RevMedx, Inc. regarding their Xstat products describe hemostatic devices for the treatment of gunshot and shrapnel wounds that work by injecting a group of small, rapidly-expanding sponges into wound cavities using a syringe-like applicator. In the wound, the sponges expand and swell to fill the wound cavity to create a temporary barrier to blood flow and provide hemostatic pressure. However, this system is not ideally set up to inject sponges throughout the abdominal cavity. It also can only access the abdominal cavity through an existing penetrating trauma wound, therefore making it of little use in the setting of blunt abdominal trauma.

U.S. Patent Publication Nos. 2011/0202016 A1 to Zugates et al. and 2012/0107439 A1 to Sharma et al. (with related U.S. Patent Publication Nos. 2013/0110066 A1 to Sharma et al.; 2012/0265287 A1 to Sharma et al.; 2009/0041824 A1 to Zugates et al.; and, 2016/0271293 A1 to Zugates et al.) describe injecting a biodegradable synthetic polymer into a body cavity together with another agent; the polymer and other agent then subsequently combine via a chemical reaction within the body cavity to produce a hardened elastomeric polymer foam, which prevents or limits bleeding. Product information from Arsenal Medical describes a hardening foam that binds to intra-abdominal tissues to reduce and stop bleeding. The provider injects two liquid polymers from a canister, via a large naked needle, into the abdominal cavity. Upon combination inside, these ingredients react to envelop and harden around the internal organs.

However, a solidified product in the abdominal cavity may cause serious medical issues for the life of the patient. Likewise, needing to cut out a large block of hardened material after use is clearly suboptimal. Additionally, the prior art does not include any safety method for medics or others in the out-of-hospital environment to deploy a synthetic polymer intra-abdominally, except for a naked needle. Insertion of a large naked needle into the abdomen, even by highly trained surgeons in a controlled operating room environment, can easily result in bowel or other intra-abdominal injury. Thus, this method is clearly suboptimal.

U.S. Patent Publication Nos. 2014/0271531 A1, 2014/0316012 A1, 2013/0317418 A1, and 2014/0271533 A1 to Freyman et al. describe injection of prepolymer that reacts with water to cause an in-situ forming polymer foam for embolizing or occluding cavities (e.g. aneurysm, lung, vessel). However, this also becomes a hard foam that is not easily reversible. It also must react with water within the body, which may result in variable response depending on the dampness of that particular body cavity. It is further described for injection into smaller lumen cavities and not those with very large volumes, such as the peritoneal cavity. U.S. Patent Publication No. 2002/0122771 A1 to Holland et al. shows a wound dressing hydrogel that can be sprayed on as a liquid and then crosslink or otherwise thicken to form a hydrogel in situ with similar limitations.

U.S. Pat. No. 8,668,899 B2 to Dowling et al. describes a sprayable polymeric foam hemostat for both compressible and non-compressible (intracavitary) acute wounds. This foam comprises a hydrophobically-modified polymer (e.g. hm-chitosan) or related amphiphilic polymers that anchor themselves within the membrane of cells in the vicinity of the wound. However, this polymer is not easily washed away and needs to be broken down before excretion from the body. Chitosan and related substances are additionally not synthetically formulated, which may lead to quality control issues and difficulty in manufacturing. Finally, this product and related hemostatic foams do not have a means for inducing physical tamponade within the body from the controllable transmission of higher pressures.

Prior art includes multiple uses of polymers for hemostasis. These include examples of gels, putties, and waxes to assist with tamponade of bleeding. Examples include U.S. Pat. No. 8,497,408 B2 to Winek et al. U.S. Patent Publication Nos. 2004/0013715A1 to Winek et al., 2003/0095945 A1 to Levey et al., 2006/0100370 A1 to Wellisz et al., 2009/0286886 A1 to Fisher et al., 2006/0193899 A1 Sawhney, 2016/0256170 A1 to Busold et al., 2003/0203044 A1 to Moravec, and U.S. Pat. No. 9,616,088 B2 to Diehn et al. However, these polymers are directly applied to the site of injury and do not foam to be sprayed on or spread throughout a body cavity.

The literature additionally discloses prior art regarding inverse thermosensitive polymers (i.e. inverse or reverse thermosensitive, thermosetting, phase, or thermally viscosifying polymers) as a means of providing hemostasis. Several publications describe use of inverse thermosensitive polymers to provide temporary embolization of a vessel via intravascular gel injection, such as U.S. Patent Publication No. 2005/0008610 A1 to Schwarz et al., 2005/0147585 A1 to Schwarz, 2011/0087207 A1 to Vogel et al, and 2008/0181952 A1 to Vogel et al. However, these do not spread via foam to provide hemostasis throughout a larger area and volume. Similarly, U.S. Patent Publication No. 2007/0191768 A1 to Kolb (with related U.S. Pat. No. 8,062,282) provides a method for occluding a body lumen by placing the tip of a catheter into a lumen, spraying thermosensitive polymer, and then withdrawing the tip. However, this requires at least partial withdrawal of the catheter tip while spraying directly in the area of interest. Likewise, U.S. Patent Publication No. 2008/0208163 A1 to Wilkie discloses the use of an inverse thermosensitive polymer to control biological fluid flow by an in situ formed polymer plug. However, this gel or solution also needs to be directly injected through a catheter to a specific site. Additionally, U.S. Patent Publication No. 2008/0031847 A1 to Cohn et al. (with related U.S. Patent Publication No. 2013/0158589) describes a method and kit for treating lacerations and puncture wounds using an inverse thermosensitive polymer. However, this polymer does not foam and is rather a liquid that becomes a gel after spraying it from a syringe or tube. These are thus not amenable to spread throughout a larger area or volume (e.g. via injection into a large body cavity, such as the peritoneal cavity).

The prior art additionally discloses multiple uses of inverse thermosensitive polymers for the delivery of different pharmaceutical agents, although not specifically utilized with foam delivery. These include U.S. Pat. No. 4,474,752 to Haslam et al. and U.S. Pat. No. 6,316,011 B1 to Ron et al., and U.S. Patent Publication No. 2011/0294760 A1 to Bahulekar et al.

Each of the patents and published patent applications mentioned above are hereby incorporated by reference.

SUMMARY OF THE INVENTION

The present invention overcomes and substantially alleviates the deficiencies in the prior art by providing improved systems and methods relating to synthetic polymer formulations.

In several embodiments, the present invention relates to systems and devices for delivering synthetic polymers to a body cavity (e.g. abdominal cavity) to reduce and/or stop bleeding. Under some of these embodiments, the synthetic polymer formulation may be provided in the form of an aqueous solution, gel, or foam. In some of these embodiments, the synthetic polymer formulation can be cleared by the body, such that there is no need for subsequent physical removal (e.g. resorbable).

In several embodiments, emergency personnel can rapidly deploy the system to deliver polymer formulation to the body to reduce or stop bleeding in the out-of-hospital or in-hospital environments, including under battlefield and mass casualty conditions.

Under some embodiments, the polymer may be used externally. Under other embodiments, an initial percutaneous access pathway into a body cavity is surgically established (e.g. laparotomy trocar, open surgical procedure) and connected to a delivery apparatus. Under other embodiments, an initial percutaneous access pathway is formed similar to the device and/or method described in U.S. patent application Ser. Nos. 13/961,422 and 14/581,339, previously incorporated by reference herein. In one of these embodiments, such a delivery device uses a probe and needle mechanism that automatically stops the advance of the device upon insertion into a body cavity or space (e.g. abdominal cavity), which minimizes user error and improves patient safety.

Under some of these embodiments, the probe of the delivery device is hollow and allows transmission of a synthetic polymer formulation with or without additional substances from a holding chamber or canister to flow through the device and hollow probe into the patient's anatomic cavity or space of interest. Under some embodiments, the polymer is initially contained within a canister, from which it is dispensed via tubing and/or other mechanism. Canisters for delivering substances under pressure are well known in the art and different embodiments utilize different types of expansion tanks, which under some embodiments contain one or more of the following features: aerosol, screw-on, easy click on, pierceable. These deliver the polymer in a pre- and/or post-foaming gel configuration. Under several embodiments, these canisters contain one or more propellent gases, as is well established in the art. Under several embodiments, the propellent gas is kept separate from the polymer to be delivered by a membrane and/or bag, so that it can transmit pressure but does not directly mix with the agent to be delivered to the body.

Under various embodiments, the synthetic polymer formulation expands once reaching the body cavity or space (e.g. abdominal cavity) to reduce and/or stop bleeding. Under some of these embodiments, the injected material does not need to chemically react inside the abdominal cavity, rather its innate properties and/or a propellant pushing the material into the cavity causes it to expand once reaching the desired space. The polymer formulation expands to partially or fully fill the cavity and provide pressure, physical tamponade, and/or deliver bioactive substances to prevent, reduce, and/or stop bleeding.

Some of these embodiments include one or more valves (e.g. control, regulator, pressure, vent, relief, head pressure, dispensing, one-way, poppet), which automatically senses the appropriate pressure and terminate the insertion of the polymer formulation into the cavity at the desired pressure. Examples include both single and double stage regulators. They can be an integral device with an output pressure setting, a restrictor and a sensor all in the one body, or consist of a separate pressure sensor, controller and flow valve. Under many embodiments, there is also a main on-off valve (e.g. ball valve) that may be manually (e.g. turning of valve lever, pushing of electronic button) or automatically (e.g. connect to a countdown clock, tied to a more complex electronic algorithm) engaged. Under some embodiments, the insertion of polymer formulation into the cavity terminates at a set volume. Under some embodiments, the system controls pressure so as to maximize hemostasis while minimizing injury from high pressure (e.g. abdominal compartment syndrome, intestinal injury, high peak lung pressure). Under various embodiments, the system allows controlled pressure to be delivered and/or maintained to a selected body area (e.g. body cavity) by the user (e.g. under manual and/or automated control). Under one example of an embodiment wherein pressure is under manual control, the user utilizes an incorporated pressure gauge to determine how much formulation and thus pressure to deliver. Under another example of an embodiment wherein pressure is under manual control, the user opens the main on-off valve of the system, which then delivers formulation to maintain a set pressure within a cavity being treated while open. Under other embodiments, the system is set for a specific pressure profile and it automatically stops delivery at a peak pressure and/or adds additional polymer at lower pressures to deliver the desired pressure profile.

For example, under some embodiments, the device delivers polymer to a body cavity to a peak pressure of 60 mmHg, at which time it automatically stops additional polymer delivery. For the first 5 minutes of delivery, the device works to maintain a pressure between 50-60 mmHg (e.g. above the patient's mean arterial pressure), delivering more polymer if the pressure falls below the lower cutoff (i.e. 50 mmHg) and stopping delivery if it reaches the maximum set (i.e. 60 mmHg). Under some embodiments, the device then has other pressure settings for one or more subsequent time periods (e.g. pressure set to 5-10 mmHg for the next 60 minutes). Under some embodiments there is additionally a pathway through a needle to remove gas and reduce the pressure if it is too high. The exact pressure and time duration settings vary under different embodiments and thus this invention is not limited to specific pressures or time periods as these can easily be changed by a person having ordinary skill in the art.

Under some embodiments, the present invention contains one or more additional substances to assist with preventing, slowing, and/or stopping bleeding. These include, but are not limited to, components of the intrinsic clotting pathway (e.g. factors XI, IX, VIII); components of the extrinsic clotting pathway (e.g. transmembrane receptor tissue factor, plasma factor, factor VII/VIIa); tranexamic acid and other amino acids and their analogs; epinephrine and other vasoconstrictors; thrombin; fibrinogen; potassium ferrate; cellulose, including oxidized and/or regenerated cellulose; kaolin; smectite granules; zeolite; chitosan; sodium carboxymethylcellulose; amylopectin; microfibrillar collagen; propyl gallate; aluminum sulfate; fully acetylated poly-N-acetyl glucosamine; related substances; and other clotting agents, platelet aggregators, and substances that reduce or stop bleeding.

Under some embodiments, the present invention contains one or more additional substances to assist with preventing, slowing, and/or stopping bacterial and/or other infections. These include, but are not limited to, antimicrobial agents (e.g. antibiotics), disinfectants (e.g. alcohols, aldehydes, oxidizing agents, phenolics, quaternary ammonium compounds, silver-based products, copper-based produces, and/or other disinfectants), and/or other agents (e.g. antifungals). Under some embodiments, a synthetic polymer with one or more of these additional substances is delivered into a body cavity. Under other embodiments, a synthetic polymer with one or more of these additional substances is sprayed or otherwise delivered to an external wound or area.

Under some embodiments, the present invention contains one or more of the previously mentioned additional substances at normal concentrations for administration in the body. Under some embodiments, the present invention contains one or more of the previously mentioned additional substances at concentrations higher than could be used via oral and/or parenteral administration because it is delivered directly to a cavity and/or space. Thus, the body cavity and/or space has a high concentration of the additional substance, but there is a lower concentration systemically or away from that cavity and/or space. This allows a high concentration at the needed site but a lower concentration away from it, which minimizes systemic and/or more distal side effects. For example, a clotting agent could be used at very high concentration when administered directly to the abdominal cavity, to cause clotting of any traumatic bleeding vessels there, when administering such a high concentration of the agent is not possible via oral and/or parenteral rout because it would cause systemic clotting of healthy vessels in the body. Similarly, an antibiotic such as gentamicin could be deployed at very high concentrations in the abdominal cavity, which if given via parenteral route would have toxic effects.

Under various embodiments, the present invention has one or more of the following characteristics: it is field-adapted with a small size, easily fitting into a medical field kit; it has a delivery device for safe and rapid deployment by medics or other non-surgeon providers; it is stable without need for refrigeration, with the ability to maintain activity under the environmental extremes experienced in military operations; it is rapidly applied to penetrate deep into intra-abdominal injuries of all shapes and sizes; it induces hemostasis; it provides a delivery mechanism for a wide range of additional bioactive clotting agents; it prevents bacterial adhesion and/or biofilm formation; it inhibits drug-resistance mechanisms in multidrug-resistant strains of bacteria; it is partially or fully resorbable by the body; it has a low risk of complications; it is not exothermic and/or has minimal risk of iatrogenic thermal injury to organs; it is transparent does not discolor the abdominal organs; it is water soluble; it may be quickly and easily washed away for easy removal if needed for emergent laparotomy surgery; it contains no toxic substances or materials with potential for adverse environmental effects; it uses expanding and/or propellant components that are non-ozone depleting; and/or it is made in whole or part from synthetic, inert polymers that are already FDA and EU-approved for pharmaceutical applications.

Under several embodiments, the synthetic polymer formulation comprises a solution of one or more copolymers of ethylene oxide (EO) and propylene oxide (PO) (e.g. in an aqueous solution), in combination with one or more volatile or gaseous expanding and/or propelling components which is dissolved in, or evenly dispersed throughout, said copolymer solution. Such copolymers may be a random or block copolymer of EO and PO having an average molecular mass of about 1 kg/mol to about 100 kg/mol, and a mass ratio of EO to PO of between 5:95 to 95:5. In some of these embodiments, the block copolymer is a poloxamer. Poloxamers are linear A-B-A triblock copolymers of EO and PO having the general formula $(EO)_x(PO)_y(EO)_x$, where x and y represent the number of EO and PO monomer units in the block. Different poloxamers having a molecular mass in the range of about 1 kg/mol to about 15 kg/mol and EO:PO ratios by mass of between 8:2 and 1:9 are commercially available, (e.g., PLURONIC® copolymers from BASF). In certain advantageous embodiments, the block copolymer is a poloxamer produced in NF grade for medical applications, and which is approved for pharmaceutical use. Examples include poloxamers P188, P237, P338 and P407, also known as Pluronic® F68, F87, F108 and F127; the ranges of molecular mass and mass % of EO (as oxyethylene) for each of these poloxamers is shown in FIG. 15.

Under several embodiments, the one or more volatile expanding and/or propelling components is a compressed gas or volatile liquid that is dissolved within or evenly dispersed throughout the polymer solution under elevated pressure. The compressed gas or volatile liquid expands and/or evaporates into a gaseous form due to the decrease in pressure as it is released from its storage container, thereby causing the polymer solution to foam (e.g. within the body cavity). This gas or volatile liquid may be any one of the many medical grade gases suitable to be delivered to the body. Under several embodiments, this gas or volatile liquid is one or more organohalide compound, such as a fluorinated hydrocarbon (i.e. hydrofluorocarbon, or HFC) or a perfluorocarbon. For example, under some embodiments, the synthetic polymer formulation is mixed with 1,1,1,2-tetrafluoroethane (i.e. norflurane, R-134a) in liquid form under a pressure of 100 pounds per square inch (psi). This mixture of polymer and hydrofluorocarbon provides a foaming polymer solution once discharged from the storage canister. Thus, under multiple embodiments, no chemical reaction with any components within the body (e.g. water) is required to cause the synthetic polymer formulation to foam.

Under several embodiments, the synthetic polymer formulation is an aqueous solution of a block copolymer (e.g. a poloxamer) of a suitable type and in an adequate concentration to exhibit reverse phase change properties, such that the solution increases markedly in viscosity (e.g. forming a strong gel when it is warmed) and decreases in viscosity when it is cooled. By selecting the type of block copolymer and an appropriate concentration in solution, this reverse phase change can be tailored to occur over a desired temperature range such that the solution is a low viscosity liquid at temperatures below that anticipated to occur in the body, for example less than about 5-10☐C but is a highly viscous gel at temperatures above about 20-30☐C.

Under many embodiments, the reverse phase properties of such a block copolymer solution provide a key advantage of the current invention, such that after delivery to the body (e.g. into the an internal cavity, sprayed externally) that the synthetic polymer formulation is as viscous as possible and have the form of a highly viscous gel in order to exert the maximum hemostatic effect by physical tamponade (i.e., by providing a physical barrier to resist the flow of blood from damaged blood vessels). However, in practice (e.g. use in acute abdominal hemorrhage) it is also necessary to deliver the solution to the patient rapidly to stop the bleeding as soon as possible and ideally through a small diameter tube or needle, which would be difficult or impossible to achieve if the solution were a highly viscous gel during delivery. The use of a synthetic polymer formulation with appropriately tailored reverse phase properties in conjunction with a suitable choice of expanding gas provides a simple solution to these conflicting requirements. In many embodiments, the reverse phase characteristics of the polymer solution and the properties of the expanding gas are arranged such that the cooling effect due to expansion of the gas as the solution is discharged ensures that the polymer solution is in low viscosity liquid form as it exits the storage container, thereby facilitating rapid delivery to the patient. After it is delivered, the body temperature of the patient causes the polymer solution to increase in viscosity, forming a highly viscous gel foam, which provides a much stronger tamponing effect than could be achieved if the polymer solution remained in the liquid form. An additional advantage of the reverse phase properties of the polymer solution is that the viscous gel can later be easily removed, if necessary, by cooling (e.g. by irrigation with cool water or normal saline within the abdominal cavity) whereupon it reverts to liquid form.

From the foregoing, it can be seen that the present invention provides systems and methods relating to synthetic polymer formulations within animals, especially humans. Moreover, it should also be apparent that the device can be made in varying lengths, sizes and capacities, and the precise composition of the synthetic polymer formulation, the amount delivered and the rate and pressure at which it is delivered may be varied appropriately to treat adults, children, and infants. While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification and that elements of certain embodiments can be combined with elements of other embodiments. Additional objects, advantages, and novel features of the invention will be set forth in the description which follows, and will become apparent to those skilled in the art upon examination of the following detailed description and figures. It should be understood that not all of the features described need be incorporated into a given system or method.

BRIEF DESCRIPTION OF THE DRAWINGS

FIG. 15 is a table showing ranges of molecular mass and mass % of EO (as oxyethylene) for NF grades of poloxamers P188, P237, P338, and P407, per USP-NF 23.

FIG. 16 is a table showing comparison of foam expansion, stability, and volume.

FIG. 17 is a table showing gelation temperature for aqueous Pluronic solutions.

DETAILED DESCRIPTION OF THE INVENTION

Figure 1:
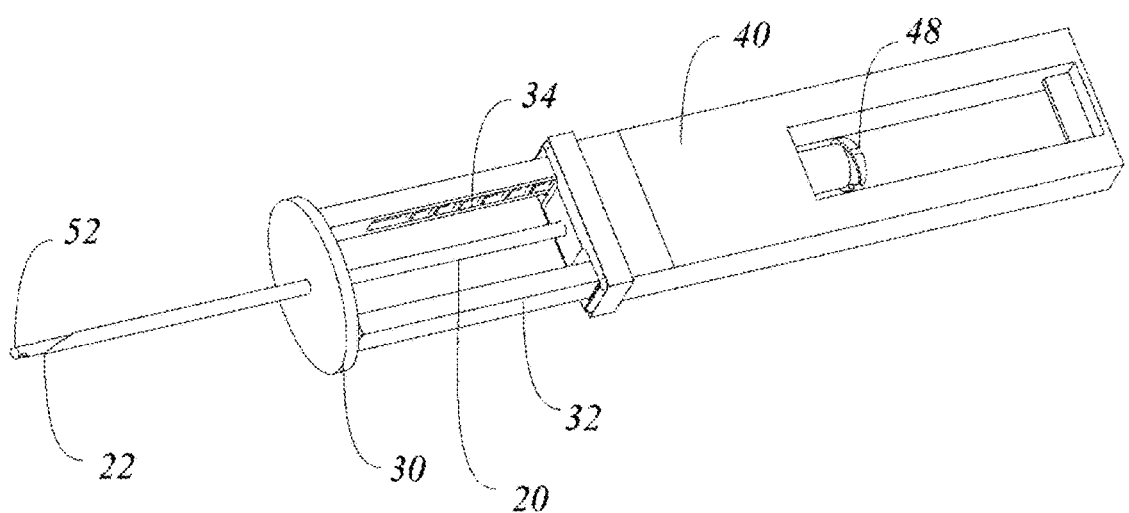
FIG. 1 is a perspective view of part of a system to deliver synthetic polymer formulations to the body in accordance with one embodiment, as assembled prior to use.
Figure 2:
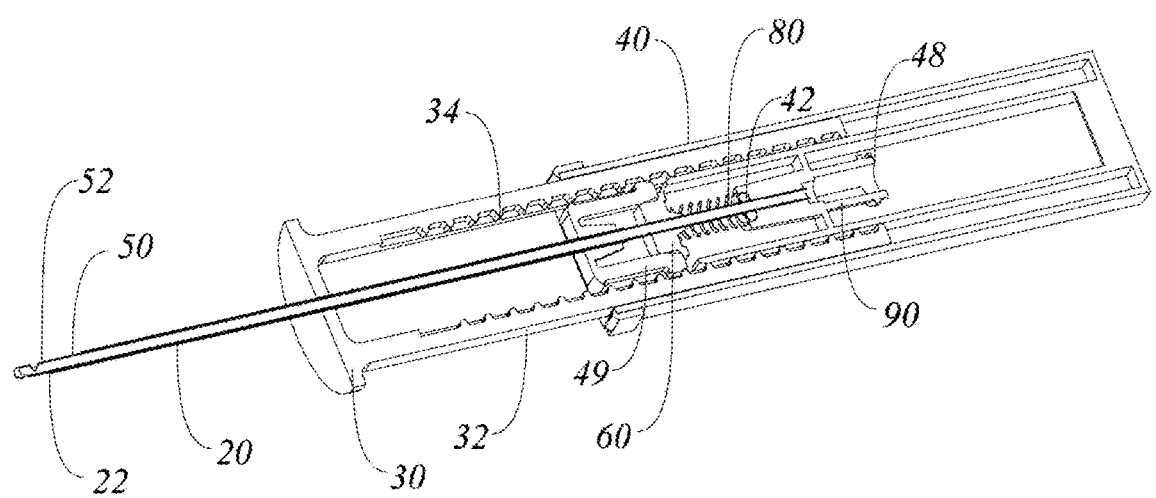
FIG. 2 is a cross section view of part of a system to deliver synthetic polymer formulations to the body in accordance with one embodiment, as assembled prior to use.

Referring to the drawings, FIGS. 1 and 2 illustrate one embodiment of part of the present invention. For ease of reference, distal shall refer to the end of the device farthest away from the user, while proximal shall refer to the end of the device closest to the user.

Under this embodiment, stabilizer 30 initially extends distally from holder 40 along the tract of needle 20, to provide a mechanism for automatically halting the forward movement of needle tip 22 and probe tip 52 upon penetration into a body cavity (e.g. peritoneal cavity). Holder 40 has one or more phalanges 49 that are resiliently biased medially, but when pushed laterally by probe holder 60 are caused to interact with grooves 34 on rods 32 so as to halt the movement of stabilizer 30 in respect to holder 40.

Biased by spring 80, in its distal position probe holder 60 extends tip 52 of probe 50 out distally from tip 22 of needle 20. Additionally, this pushes phalange(s) 49 laterally to reversibly lock with grooves 34 and inhibit the movement of rod(s) 32 and thus stabilizer 30 in relation to the rest of device 10.

When needle 20 pierces the skin and enters into a cavity (e.g. peritoneal cavity), probe tip 52 to moves proximally in reference to needle tip 22. This causes holder 60 on probe 50 to also move proximally in reference to housing 40. This in turn allows phalanges 49, which are biased medially, to move medially and thus unlock from groove(s) 34 to allow rod 32 and thus stabilizer 30 to move in relation to housing 40. Thus, when a general distal biasing of the device is provided by the user, stabilizer 30 remains flush with skin of the body while the rest of the device moves distally, thus inserting needle 20 further into the cavity.

Once probe tip 52 and needle tip 22 have reached a body cavity, spring 80 is free to move probe tip 52 distally in reference to needle tip 22, which allows holder 60 to move distally in reference to housing 40 and thus forces phalange(s) 49 laterally to again lock with grooves 34 and inhibit the movement of rod(s) 32 and thus stabilizer 30 in relation to housing 40. This, in turn, prevents needle tip 22 from moving further into the cavity, thus minimizing the chances of injuring vital structures. Under one embodiment, there is an airtight seal between probe 50 and housing hole 42, which may include the use of an O-ring and/or other sealing mechanisms.

When probe tip 52 has entered the cavity, there is then a contiguous pathway between connection port 90 with luer lock groove 48 through the device and into probe tip 52. Reversibly or irreversibly connected to connection port 90, in some embodiments via standard luer lock, is a standard, high-pressure, tapered, or otherwise configured tube (not shown) from a delivery container, such as one shown in FIG. 3, 4, or 5 and described below. Thus, when deployment is initiated, polymer formulation (e.g. as a partial or complete liquid, or as foam) is dispensed from the delivery container, travels through the connection tubing, and proceeds through the continuous pathway within the portion of the device shown in FIGS. 1 and 2 to be dispensed into the body cavity of interest.

Figure 3:
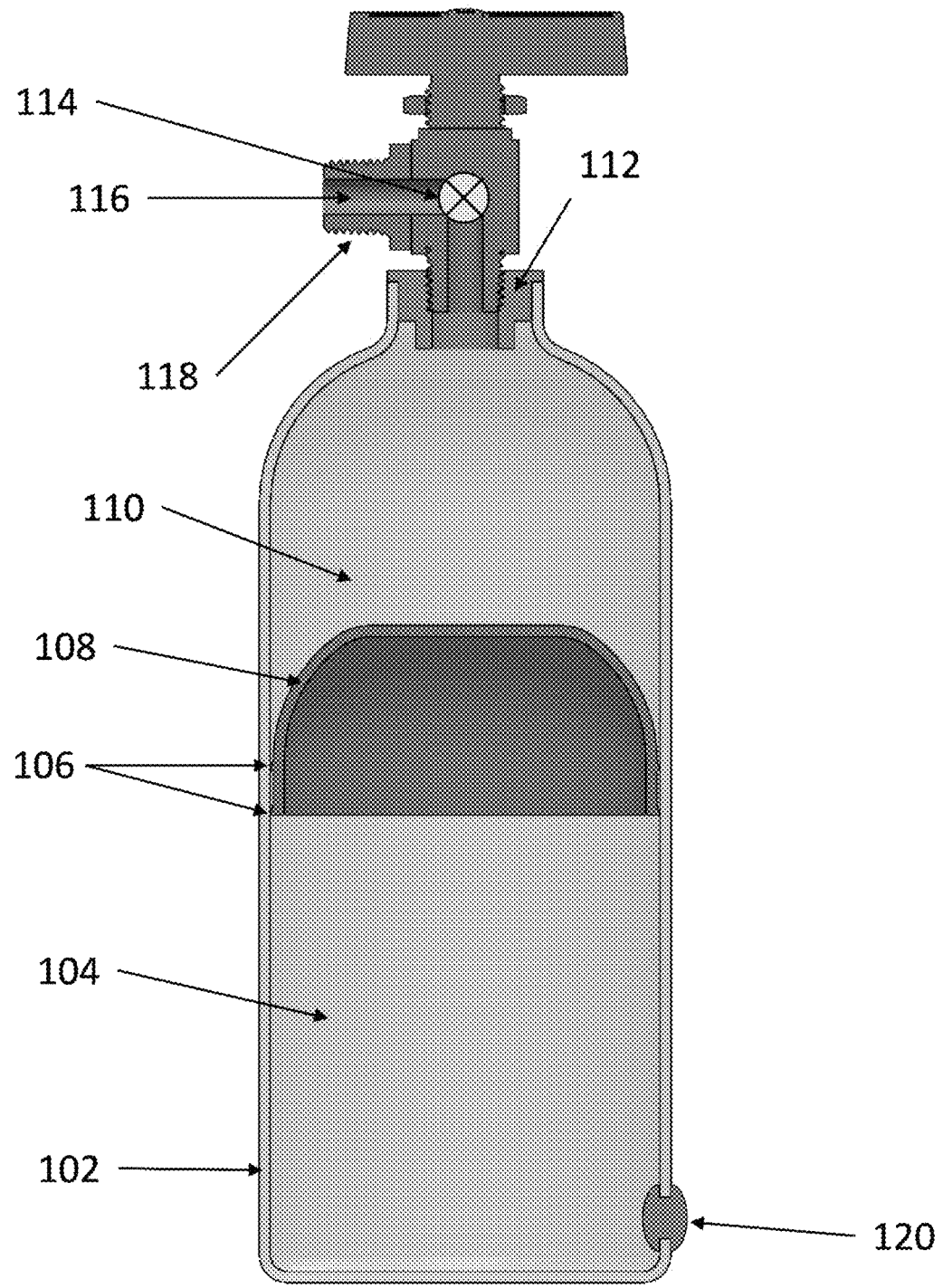
FIG. 3 is a cross section view of part of a system to deliver synthetic polymer formulations to the body in accordance with one embodiment, as assembled prior to use.

FIG. 3 illustrates a delivery container suitable for holding and delivery of the synthetic polymer formulation under one embodiment. The body of the delivery container consists of a pressurizable vessel 102 with a closure 112 containing a suitable release valve mechanism 114. The vessel, closure, and release valve can withstand an internal pressure (e.g. up to 200 pounds per square inch). Internally, the vessel is divided into an upper space 110, and a lower space 104, by a freely-moving piston 108. The piston 108 bears a pressure-tight seal 106 that prevents movement of liquid or gas from one space into the other. The seal 106 may be integral to the piston or may be created using a separate sealing component such as an O-ring. The release valve mechanism opens into an exit nozzle 116 which has an appropriate means (illustrated in FIG. 3 as a male threaded connector 118 as an example) to attach the delivery container to a suitable delivery device (e.g. the device illustrated in FIGS. 1 and 2 via the aforementioned tubing and described above). The vessel also contains a gas-tight valve 120 or other similar means to allow a gas or volatile liquid to be introduced into the lower space 104. When the delivery container is fully assembled and ready for use, the upper space 110 contains the synthetic polymer formulation optionally mixed with a first compressed gas or volatile liquid (the "expanding gas") which causes the synthetic polymer formulation to foam when released from the delivery container. The lower space 104 contains a second gas or other highly volatile liquid (the "driving gas"). The driving gas may be either be introduced into the lower space of the delivery container prior to use (e.g. at the time the container is initially filled with the synthetic polymer formulation) or it may be introduced into the lower space of the delivery container at the time of use (e.g. by connection to an external source such as compressed air supply or a pressurized gas cylinder).

A key feature of this embodiment is that the driving gas in the lower space 104 is physically separated from the synthetic polymer formulation in the upper space 110. An advantage of this embodiment is that the pressure of the driving gas in the lower space 104 can be arranged to always exceed the pressure of the expanding gas in the upper space 110 until the contents of upper space 110 have been sufficiently discharged from the container, thereby maintaining the expanding gas in a compressed form until the synthetic polymer formulation has been released via the valve mechanism 114 into the exit nozzle 116.

Figure 4:
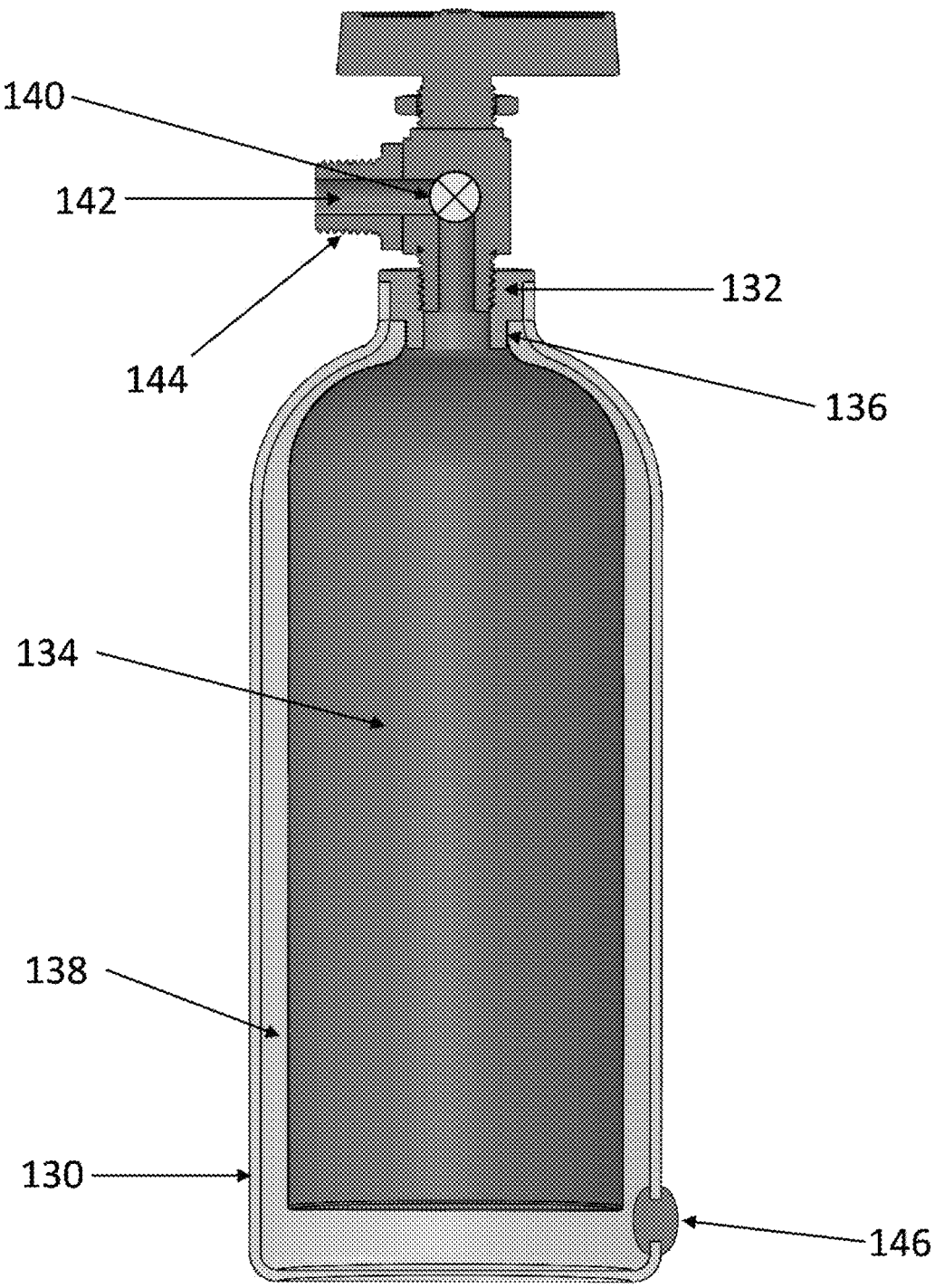
FIG. 4 is a cross section view of part of a system to deliver synthetic polymer formulations to the body in accordance with one embodiment, as assembled prior to use.

FIG. 4 illustrates a delivery container suitable for holding and delivery of the synthetic polymer formulation under another embodiment. The body of the delivery container consists of a pressurizable vessel 130 with a closure 132 containing a suitable release valve mechanism 140 and rated for an internal pressure (e.g. up to 200 pounds per square inch). A flexible, gas impermeable bag 134 is attached with a gas-tight seal 136 to the closure 132, thereby separating the inside of the vessel into two separate spaces. One of said spaces is the interior of the bag 134; this "internal space" communicates with the exit nozzle 142 via the release valve mechanism 140. The other space, "external space" 138, is the actual or potential space between the outside of the bag 134 and the inside wall of the vessel 130. The release valve mechanism 140 opens into an exit nozzle 142 with an appropriate means (illustrated in FIG. 4 as a male threaded connector 144 as an example) which allows the delivery container to be attached to a suitable delivery device such as described above. The vessel also contains a gas-tight valve or 146 or other similar means, such as a gas-tight elastomeric septum, to allow a gas or volatile liquid to be introduced into the external space 138. When the delivery container is fully assembled and ready for use, the bag 134 contains the synthetic polymer formulation optionally mixed with an expanding gas which causes the synthetic polymer formulation to foam when released from the delivery container. The external space 138 contains a second gas or other highly volatile liquid (the "driving gas"). The driving gas may be introduced into the external space of the delivery container 138 via the valve or septum or other means 146 either prior to use, (e.g. at the time the container is initially filled with the synthetic polymer formulation) or alternatively at the time of use (e.g. by connection to an external source such as compressed air supply or a pressurized gas cylinder). This embodiment shares a key feature to that shown in FIG. 3, namely that the synthetic polymer formulation expanding gas is physically separated from the driving gas, such that the pressure of the driving gas outside of the bag can be arranged to always exceed the pressure of the expanding gas in the upper space until the contents of the discharged from the container, thereby maintaining the expanding gas in a compressed form until the synthetic polymer formulation has been released via the valve mechanism 140 into the exit nozzle 142.

Figure 5:
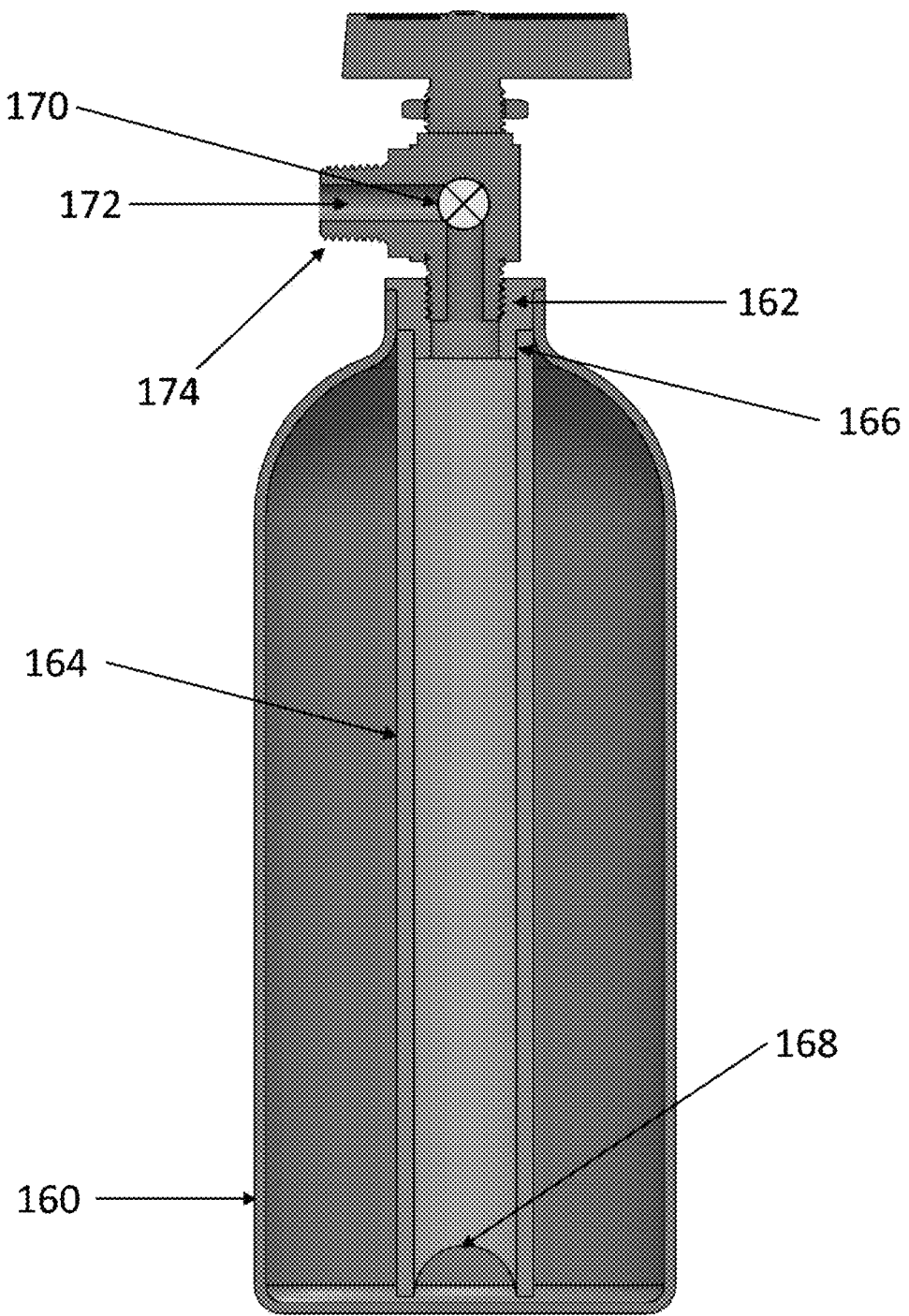
FIG. 5 is a cross section view of part of a system to deliver synthetic polymer formulations to the body in accordance with one embodiment, as assembled prior to use.

FIG. 5 illustrates a container suitable for holding and delivery of the synthetic polymer formulation under another embodiment. The body of the delivery container consists of a vessel 160 with a closure 162 containing a suitable release valve mechanism 170 and can hold an internal pressure (e.g. up to 200 pounds per square inch). The release valve mechanism opens into an exit nozzle 172 with an appropriate means (illustrated in FIG. 5 as a male threaded connector 174 as an example) which allows the delivery container to be attached to a suitable delivery device such as described above. A "dip-tube" 164 is attached via a gas-tight connection 166 to the closure 162 and extends towards the bottom of the vessel. The dip tube is designed to ensure that the lower end 168 always remains open during use, by using a tube slightly shorter than the internal height of the vessel below the closure, or by making a cut-out in or near to the end of the tube. When the delivery container is fully assembled and ready for use, the vessel contains the synthetic polymer formulation mixed with a compressed gas or volatile liquid. In this embodiment, when the release valve is opened, the compressed gas or volatile liquid initially expands or evaporates to expel the synthetic polymer solution from the container, and subsequently also causes the synthetic polymer solution to foam once it has been released via the valve mechanism 170 and enters the exit nozzle 172. Unlike the embodiments described in relation to FIGS. 3 and 4, this embodiment does not employ a physically separate expanding gas and driving gas. Instead a compressed gas or volatile liquid either contained within or in contact with the synthetic polymer formulation propels the formulation out of the delivery container. In some variations of this embodiment, the compressed gas or volatile liquid causes the synthetic polymer formulation to foam after it has been dispensed from the container.

Under some embodiments, the synthetic polymer formulation is delivered by opening the releasing valve by pushing a button, pulling a tab, or other manually-activated releasing mechanism. Under other embodiments, the delivery of the synthetic polymer formulation may be controlled automatically or semi-automatically by sensing when the probe has entered the cavity space, or in response to absolute pressure or changes in pressure within the cavity (e.g. by a sensor mechanism within the cavity itself or connected to the dispersal path earlier within the system). Such control mechanisms may be used to initiate the delivery of the polymer formulation, to override user-activated delivery under some circumstances (e.g. stopping delivery after a certain amount of time), and/or to control the polymer formulation flow rate or the maximum or minimum pressure developed within the body cavity (e.g. through a regulator mechanism). Such control mechanisms may also allow for adjustment of the pressure developed within the body cavity by administering additional polymer formulation or by venting any excess, either manually or in an automated manner under feedback control.

Some of these embodiments include one or more valves (e.g. control, regulator, pressure, vent, relief, head pressure, dispensing, one-way, poppet), which automatically sense the appropriate pressure and terminate the insertion of the polymer formulation into the cavity at the desired pressure. Examples include both single and double stage regulators. They can be an integral device with an output pressure setting, a restrictor and a sensor all in the one body, or consist of a separate pressure sensor, controller and flow valve. Under many embodiments, there is also a main on-off valve (e.g. ball valve) that may be manually (e.g. turning of valve lever, pushing of electronic button) or automatically (e.g. connect to a countdown clock, tied to a more complex electronic algorithm) engaged.

Under some embodiments, the delivery container is partially or completely integrated into the delivery device, to minimize parts.

EXAMPLES

The following examples more particularly describe certain embodiments of the invention but are intended for illustrative purposes only, since modifications and variations will be apparent to those skilled in the art.

For a series of experiments to study the physical properties of the foaming synthetic polymer formulation (Examples 1 and 2 below), a delivery container (FIG. 6) was constructed having clear walls to enable direct visualization of the polymer formulation. The delivery container shown in FIG. 6 has the same design and components as illustrated and described in FIG. 3, with the addition of a stirring paddle 122 within the upper space attached to a rotating shaft 126, which communicates with the exterior of the container via a pressure-tight rotary seal 124. This arrangement allows the synthetic polymer formulation and the compressed gas or volatile liquid (the expanding gas) to be added to the container sequentially and then mechanically stirred and mixed together within the container by rotating the shaft 126.

Example 1: Preparation of Foaming Poloxamer Formulations

Figure 6:
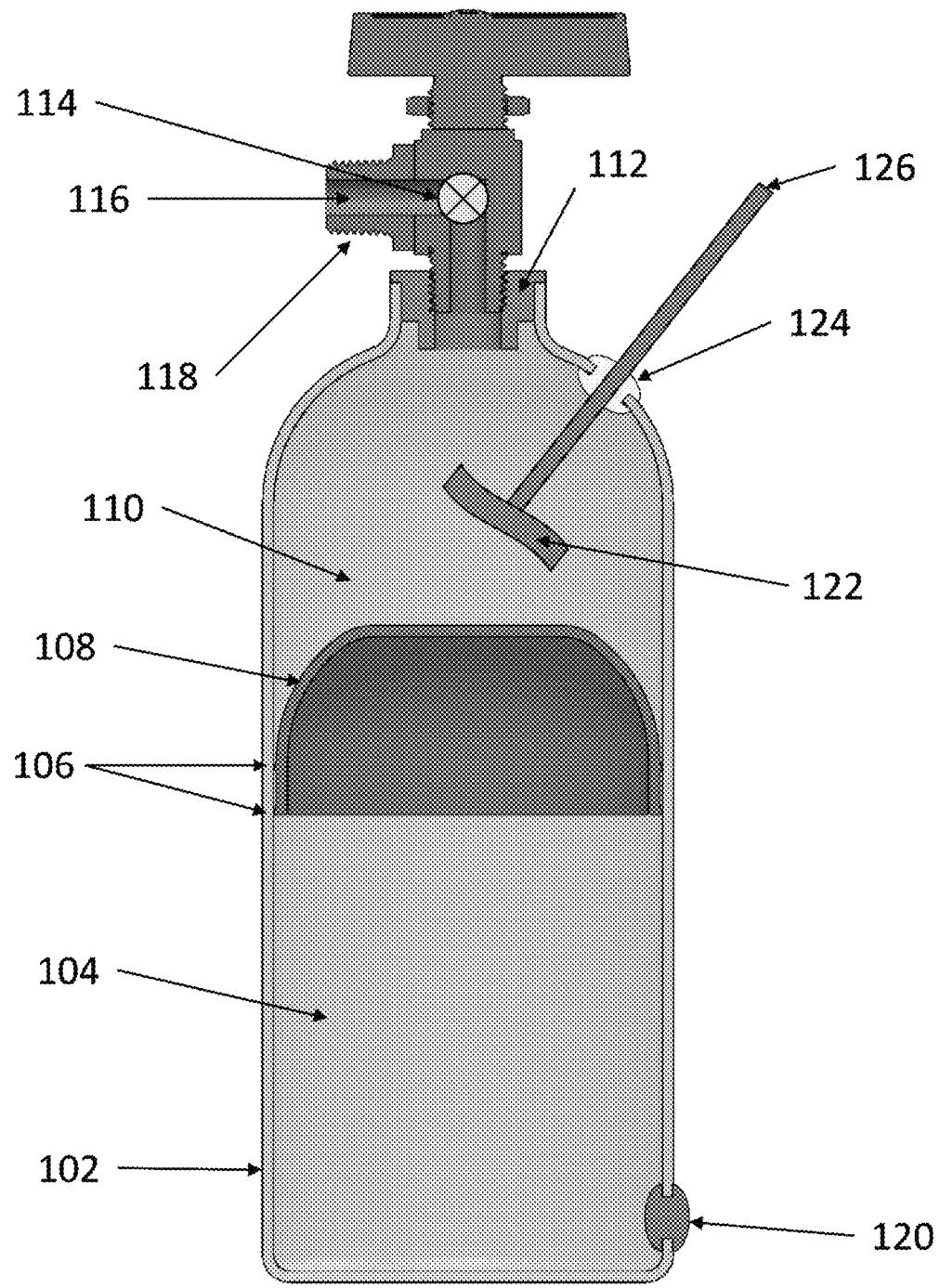
FIG. 6 is a cross section view of part of a system to prepare and to deliver synthetic polymer formulations to the body in accordance with one embodiment, as assembled prior to use.

Aqueous solutions of poloxamers P188, P338, and P407 (Pluronic® F68, F108, and F127 respectively) at concentrations from 25% w/w to 45% w/w were blended with from 2.5% to 10% by weight of 1,1,1,2-tetrafluoroethane (aka Norflurane, HFC-134a) in liquid form under pressure using a delivery container with the design illustrated in FIG. 6 and described above. The general method for preparation of every formulation was as follows:

Preparation of Poloxamer Solutions:

Reverse osmosis purified water was chilled in a laboratory refrigerator to approximately 4° C. before use. The required mass of chilled water was first weighed into a suitable laboratory pail and the calculated amount of poloxamer was then slowly added to the pail under constant mixing using a high-shear mechanical stirrer. After all the poloxamer had been added, a lid was placed onto the pail and it was transferred to a refrigerator. Periodically, the pail was removed from the refrigerator and the contents were re-mixed using the mechanical stirrer, after which it was returned to the refrigerator. The process was repeated until the poloxamer was completely dissolved, which required up to 2 days for the highest concentration solutions.

Filling of Delivery Container:

Poloxamer solution: Both delivery container valves 114 (upper valve) and 120 (lower valve) were opened and positive air pressure was applied to the upper valve to cause the piston to move to the bottom of the container. The delivery container was placed on a balance and tared. Approximately 450 mL of the cold poloxamer solution (at approximately 4° C.) was then added to the upper space 110 of the delivery container through the upper valve, and the total mass of the added solution was recorded. A positive air pressure was then applied via the lower valve to move the piston upwards sufficiently to expel any remaining air from the upper space, after which both valves were closed.

1,1,1,2-tetrafluoroethane: A pressurized cylinder of 1,1,1,2-tetrafluoroethane (TFE) was attached to the exit nozzle 116 via a length of flexible high-pressure tubing, and the delivery container was replaced on the balance and tared again. The upper valve of the delivery container was then opened, and liquid 1,1,1,2-tetrafluoroethane was dispensed slowly from the pressurized cylinder until the desired mass of TFE had been transferred into the delivery container. The upper valve was then closed, and the delivery container was pressurized to 100 psi with air via the lower valve to ensure that all the added TFA, which has a vapor pressure of 71 psi at 20°C, was compressed back into liquid form.

Mixing of Poloxamer Solution and TFE:

After both the cold poloxamer solution and the TFE were added, they were mixed together under pressure using the stirring paddle 122 attached to an electric drill. During mixing, care was taken to ensure the temperature always remained below the gelation temperature for the species of poloxamer being used and its concentration in solution (FIG. 17). The two components, both initially clear liquids, rapidly blended together to form a macroscopically homogeneous emulsion that has a much higher viscosity than either individual component. (Note that the contents remained below the gelation temperature of the poloxamer solution throughout the mixing process). Mixing appeared to be complete within 2-3 minutes; no further change was noticeable with prolonged stirring. As far as could be observed though the clear walls of the container the mixture showed no tendency to phase separate for up to 3 months of refrigerated storage. Since TFE is poorly soluble in water, the ease of mixing, and the homogeneity and stability of the resulting blend were unexpected and were presumably due to the amphiphilic properties of the poloxamer. The results of the blending process were qualitatively the same for each of the poloxamers evaluated, regardless of the poloxamer concentration, and for all proportions of TFA from 2.5% to 10% w/w.

Example 2: In Vitro Evaluation of Foaming Poloxamer Formulations

Figure 7:
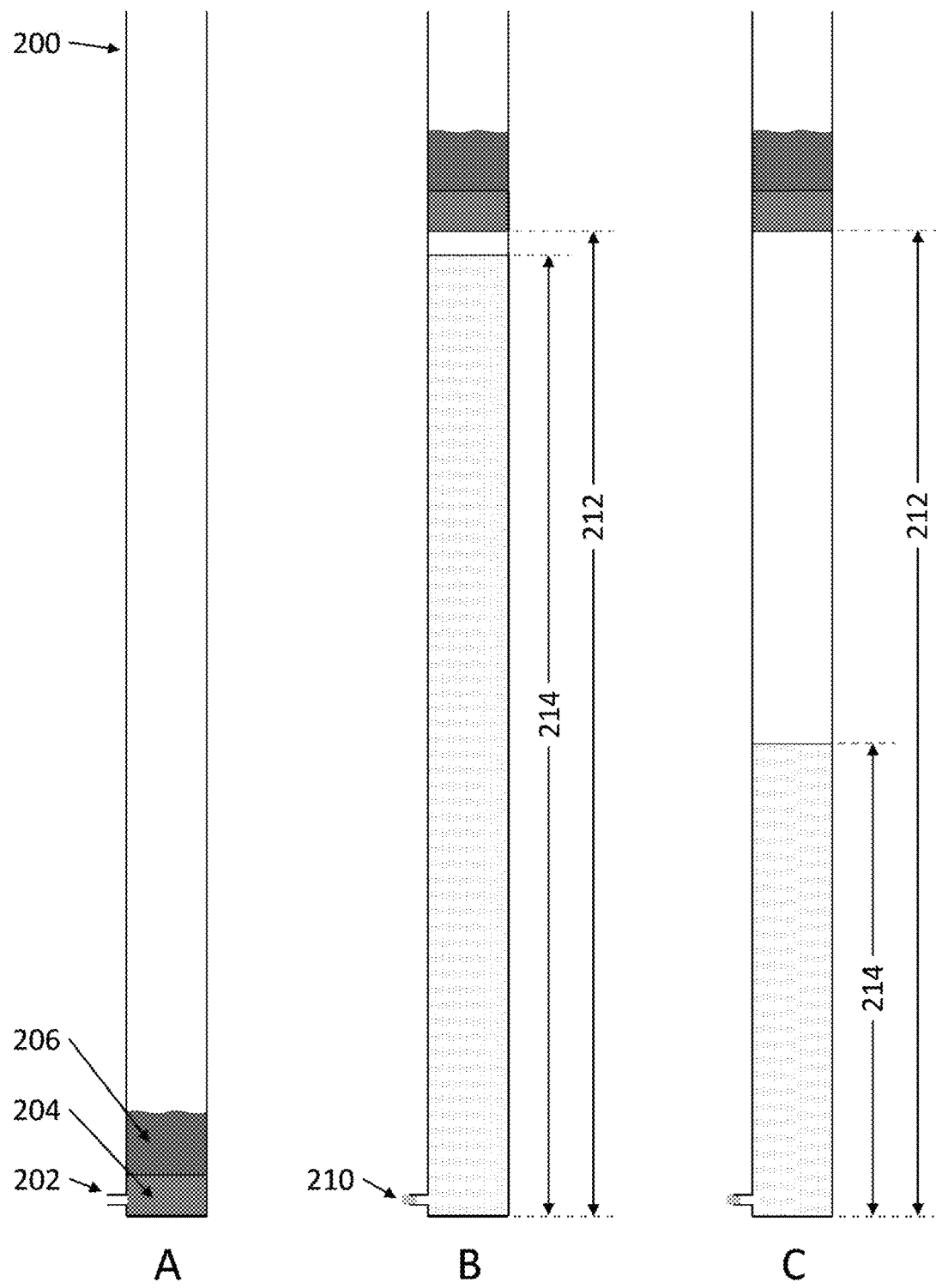
FIG. 7 is a diagrammatic representation of the foam testing apparatus used to evaluate synthetic polymer formulations to the body in accordance with certain embodiments.

Foam Height Testing: The volume and stability of the foam produced by each foaming polymer formulation was assessed using a simple foam height testing apparatus as shown in FIGS. 7A, 7B, and 7C. The apparatus (FIG. 7A) consists of a vertically mounted 120 cm high and 6.06 cm internal diameter clear polycarbonate tube 200. The lower end of the tube is sealed except for a 1 cm diameter input port 202 through which the foam is introduced. The tube contains a piston of negligible mass 204 which seals the tube, but which can move freely up and down. A column of water 206 is layered above the piston, the height of which provides a reproducible and easily measured pressure against the expansion of the foam.

In use, the delivery container was attached via a flexible tube to the port 202 and the foaming polymer formulation was introduced into the testing apparatus after which the input port was closed (FIG. 7B). The expanding column of foam caused the piston to rise until it reached a maximum height, at which time (t=0) the piston height 212 and height of the foam column 214 was recorded. The precise mass of foaming polymer formulation added to each tube was measured by weighing the delivery container before and after the polymer formulation was dispensed. After the initial expansion, the foam column slowly collapsed leaving just expanding gas in the upper region of the tube as shown in FIG. 7C. The height of the foam column 214 and the piston height 212 was measured at regular intervals for up to four hours after t=0. To normalize the data for the precise amount of polymer formulation that was dispensed for each experiment, two values were calculated for each time point; the Foam Ratio, which is the height of foam column divided by the total piston displacement (i.e., the height of the foam column plus the height of the gas-filled space above the foam), and the Specific Volume, which is the volume of the foam column (i.e., the height of the foam column x the cross-sectional area of the tube) divided by the total mass of the polymer formulation added to the tube.

Test Design: The principal goal of the experiments presented herein was to evaluate the potential utility of the foaming polymer formulations to control noncompressible hemorrhage within a specific body cavity (i.e. noncompressible intra-abdominal hemorrhage within the peritoneal cavity). Therefore, the height of the water column (and hence the pressure resisting the expansion of the foam) was set at approximately 13.5 cm to simulate the upper limit of normal intra-abdominal pressure (i.e. approximately 10 mmHg). For all studies TFA was used as the expanding gas. Each polymer formulation was evaluated in triplicate.

Presentation of Data: Example results from the foam height testing are shown in graphical form in FIGS. 8-13 and are summarized numerically in FIG. 16.

In each Figure, the upper graph shows the Foam Ratio (FR) over time for a two-hour period. Each foaming polymer solution rapidly expanded after it was dispensed into the tube, reaching a maximum foam height within 0-2 minutes, after which the foam height gradually declined over time. For a numerical comparison, the maximum Foam Ratio ($FR_{Peak}$) and the Foam Ratio after 60 minutes ($FR_{60}$) were recorded; these data are shown in FIG. 16. Since the Foam Ratio represents the proportion of the expanding gas within the foam at any time point, $FR_{Peak}$ shows the proportion of gas that is initially incorporated into the foam, while $FR_{60}$ is a measure of the collapse of the foam over time. The percentage ratio of $FR_{60}$ to $FR_{Peak}$ relates the height of the foam after 60 minutes compared to the peak foam height and is therefore an indicator of foam stability (Foam Stability Index, FSI).

The lower panel of each Figure shows the Specific Volume (SV) of the foam over the two-hour observation period. SV is a measure of the total volume of the foam normalized for the mass of the formulation that was dispensed and is therefore a function of both the overall volume of the expanding gas and the proportion of the expanding gas that is contained within the foam at any given time. For highly stable foams, the SV will increase slightly over time as the system reaches equilibrium temperature and the total gas volume continues to slowly expand. In contrast, for poorly-stable foams the SV decreases over time because the rate of collapse exceeds any increase in volume due to thermal effects. (Note that the FR is a ratio of the total foam volume to the total gas volume and therefore is not affected in the same way by changes in temperature). For a numerical comparison, the maximum Specific Volume ($SV_{Peak}$) and Specific Volume after 60 minutes ($SV_{60}$) are shown in FIG. 16.

Figure 8:
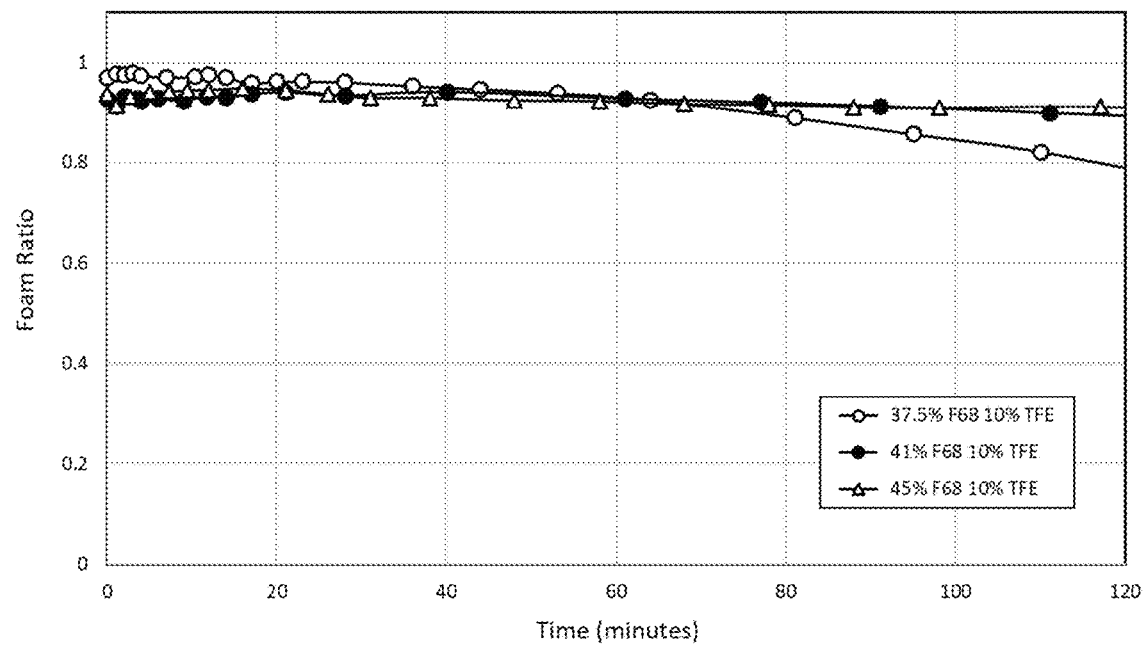
FIG. 8 is a comparison of foaming polymer formulations containing Pluronic F68 in aqueous solution (37.5%, 41%, and 45% w/w) blended with 10% w/w 1,1,1,2-tetrafluoroethane (TFE).
Figure 8:
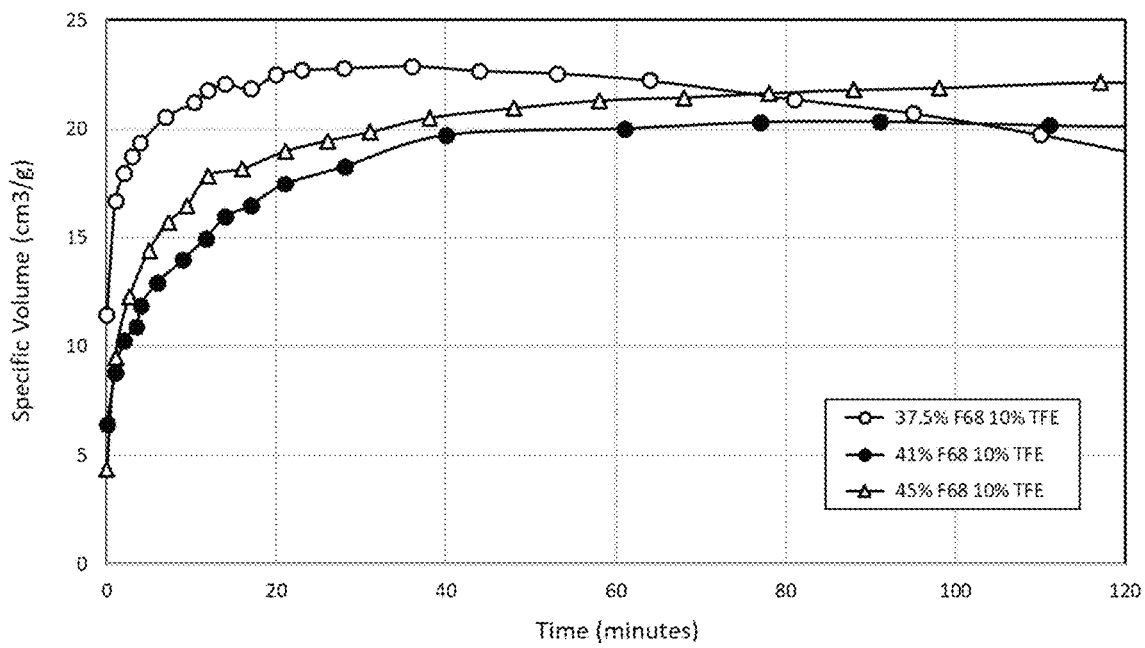

Results: FIG. 8 shows the results for Pluronic F68 solutions at three different concentrations, 37.5%, 41%, and 45% w/w. After dispensing, each formulation rapidly filled the tube with a fine-textured foam containing small evenly-sized bubbles. The $FR_{Peak}$ values (FIG. 16) ranged from 0.94 to 0.96, indicating that 94% to 96% of the expanding gas was initially entrapped within the foam. For all three concentrations of Pluronic F68, the foams were stable and subsided only very slowly over the two-hour observation period, as evidenced by $FR_{60}$ values from 0.89 to 0.92, and a corresponding Foam Stability Index (FSI) of 92%-98%. The SV values were also similar for all three concentrations tested, ranging from 21 to 25.5 cm³/gram.

Figure 9:
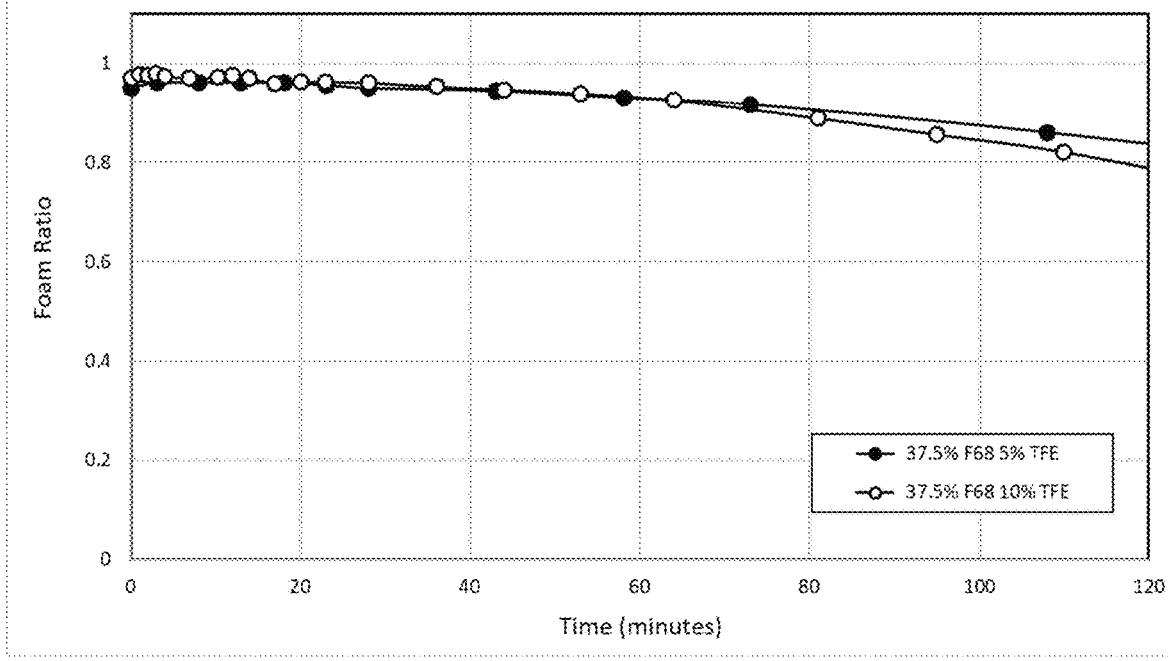
FIG. 9 is a comparison of foaming polymer formulations containing Pluronic F68 in aqueous solution (37.5% w/w) blended with 5% and 10% w/w TFE.
Figure 9:
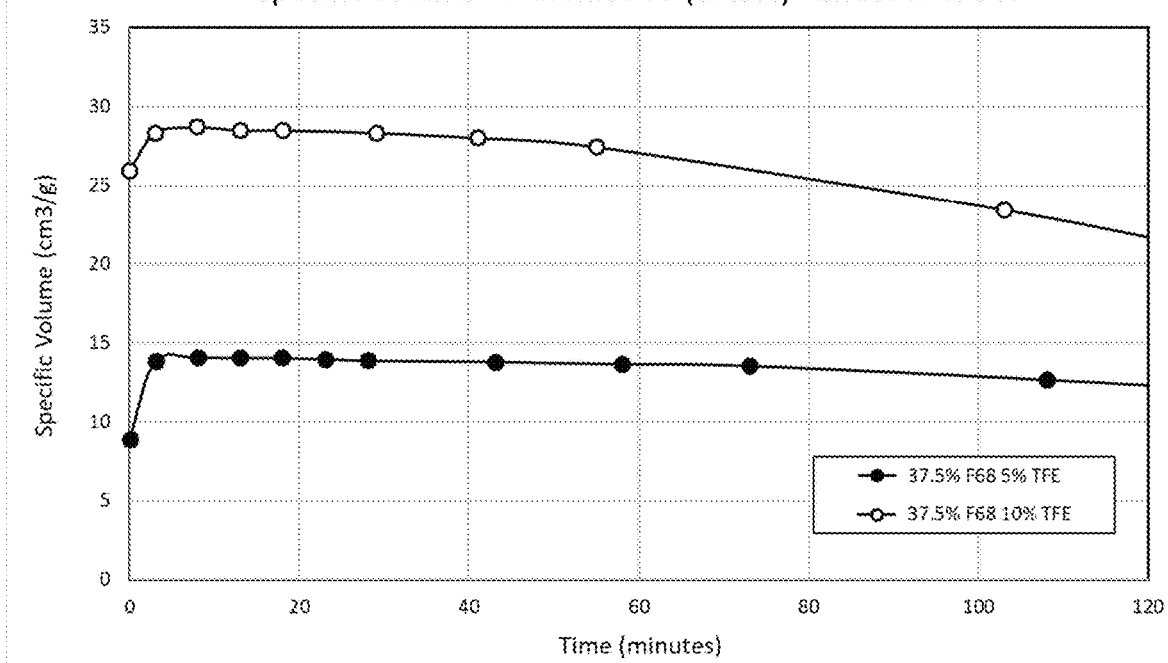

The effects of using a different proportion of TFE to expand the foam is illustrated in FIG. 9. For these experiments a 37.5 w/w Pluronic F68 solution was blended with either 5% or 10% by weight of TFE. With either amount of TFE, the initial FR and the change in FR over time were almost identical (upper panel) indicating that a similar proportion of the total gas volume was entrapped within the foam. The SV for the 10% TFE formulation, however, was approximately double that of the 5% TFE formulation.

Figure 10:
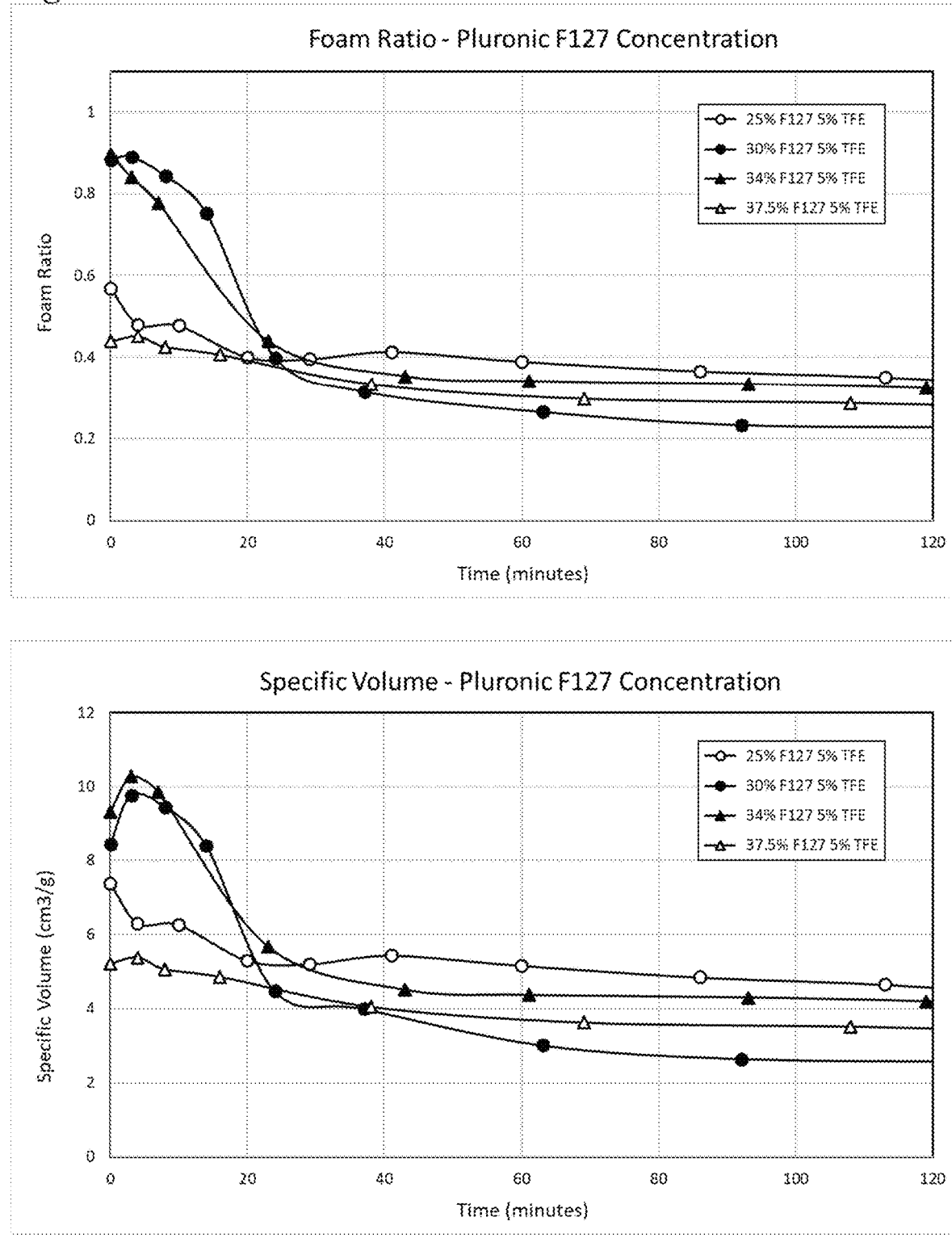
FIG. 10 is a comparison of foaming polymer formulations containing Pluronic F127 in aqueous solution (25%, 30%, and 37.5% w/w) blended with 5% w/w TFE.
Figure 11:
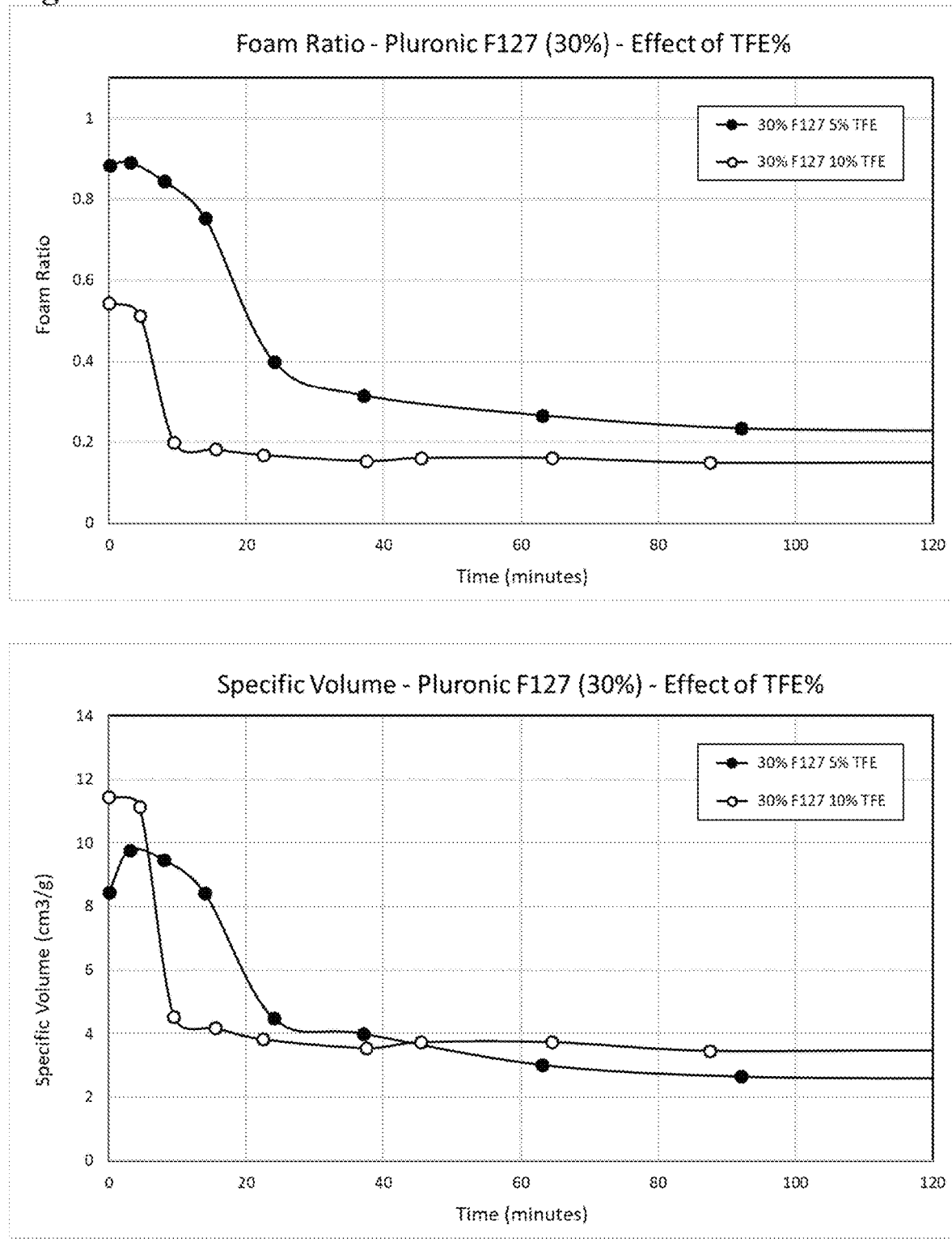
FIG. 11 is a comparison of foaming polymer formulations containing Pluronic F127 in aqueous solution (30% w/w) blended with 5% and 10% w/w TFE.

As shown in FIGS. 10 and 11, the results obtained using Pluronic F127 were quantitatively and qualitatively different from those obtained for Pluronic F68. FIG. 10 shows the results for Pluronic F127 solutions at four different concentrations, 25%, 30%, 34%, and 37.5% w/w blended with 5% by weight TFE. The lowest (25%) and highest (37.5%) concentrations produced foams that only partially filled the tube when first dispensed; for these concentrations the $FR_{Peak}$ values of 0.57 and 0.44 indicate that a large proportion of the TFE was not incorporated into the foam as it formed. The two intermediate concentrations, 30% and 34%, produced a foam that initially filled most of the tube ($FR_{Peak}$ of 0.90-0.91) but which quickly collapsed. For all concentrations, the FR fell to about 0.4 within about 20 minutes. The Foam Stability Index for the 30% and 34% w/w Pluronic F127 formulations was 26% and 38% respectively, much lower than was observed for the Pluronic F68 formulations. The FSI was not calculated for the two formulations which failed to expand properly initially. The SV values observed for the Pluronic F127 solutions were consistent with the limited expansion and reduced stability of the foam as shown by the FR data, and do not provide significant further information.

The effects of using a different proportion of TFE to expand the Pluronic F127 foam is illustrated in FIG. 11. For these experiments a 30% w/w Pluronic F127 solution was blended with either 5% or 10% by weight of TFE. In marked contrast to the results for Pluronic F68 (FIG. 9), the formulation containing 10% TFE did not expand fully, reaching a $FR_{Peak}$ of only 0.54 compared to 0.91 for the 5% TFE formulation. This result suggests that the volume of gas present exceeded the maximum amount that could be retained in the foam as it formed. This idea is supported by the SV data: the $SV_{Peak}$ for the 10% TFE formulation was 11.4 cm³/g compared to 9.2 cm³/g for the 5% TFE formulation, indicating that only about 20% of the additional TFE had been incorporated into the foam.

Visual inspection of the foams was consistent with the experimental findings: the Pluronic F68 formulations produced homogeneous-looking foams with small uniform bubbles, whereas those produced using Pluronic F127 at all concentrations had a more heterogeneous structure, with significant variability in the size of the bubbles and occasional voids.

Figure 12:
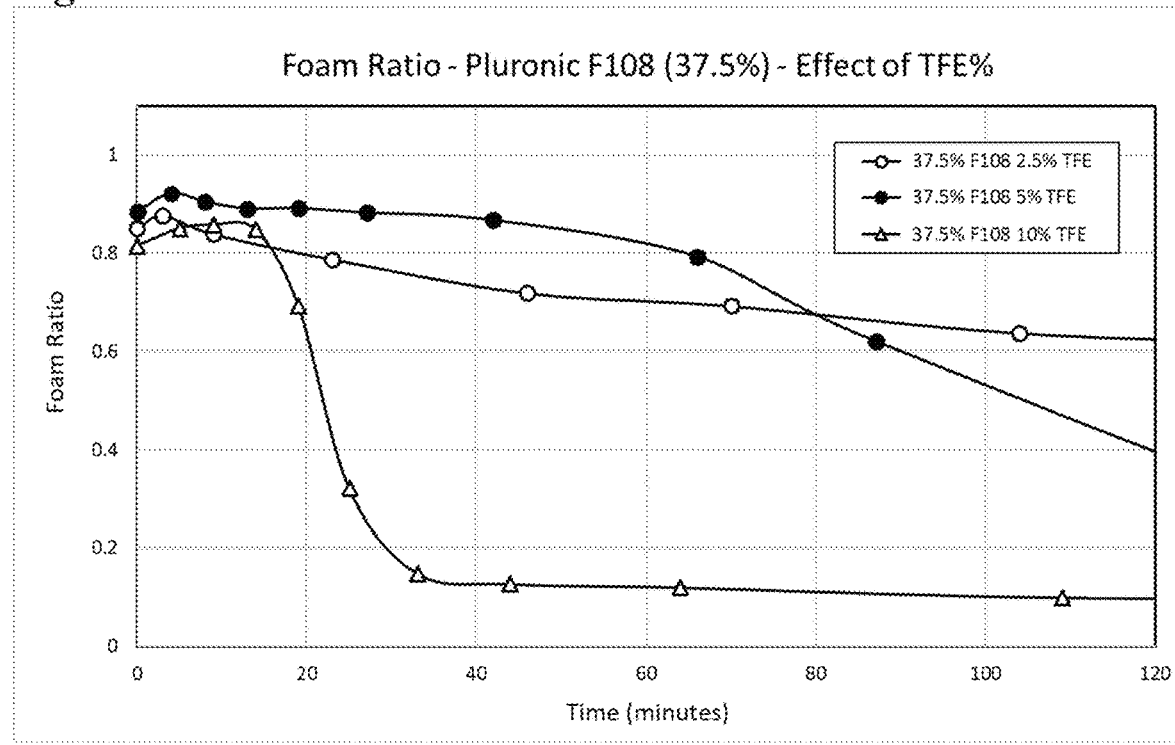
FIG. 12 is a comparison of foaming polymer formulations containing Pluronic F108 in aqueous solution (37.5% w/w) blended with 2.5%, 5%, and 10% w/w TFE.
Figure 12:
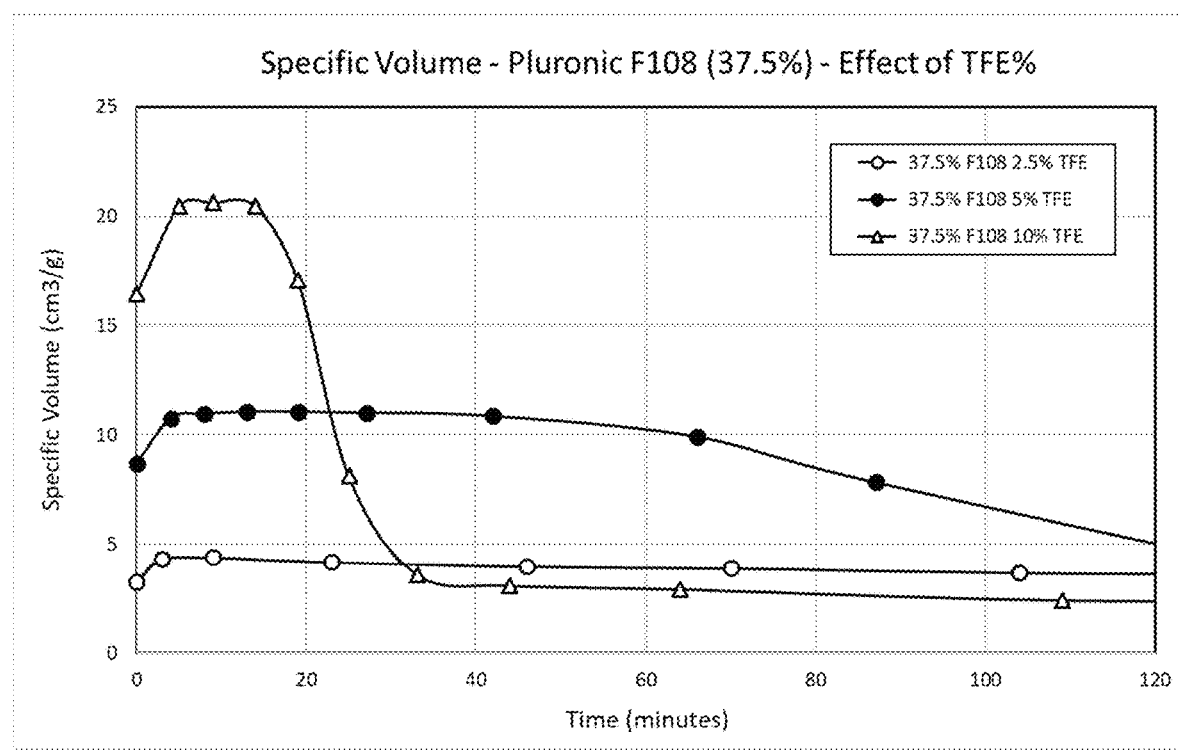

FIG. 12 shows the data for Pluronic F108 at 37.5% w/w with different proportions of TFE in the blend—2.5%, 5%, and 10%. Each formulation initially produced a (visually) good-quality foam which expanded to fill most of the tube. $FR_{Peak}$ ranged from 0.86 to 0.92. The foams remained stable for about 15 minutes. By 20 minutes the 10% TFE foam collapsed quickly, reaching a FR of about 0.12 by 40 minutes. In contrast the 2.5% and 5% TFE foams subsided relatively slowly. The difference in stability is captured in the FSI values. The SV graphs show that each formulation initially expanded to approximately the expected volume based upon the TFE content: $SV_{Peak}$ was 4.2, 11.1, and 20.6 cm³/g for the 2.5%, 5%, and 10% TFE formulations respectively.

Figure 13:
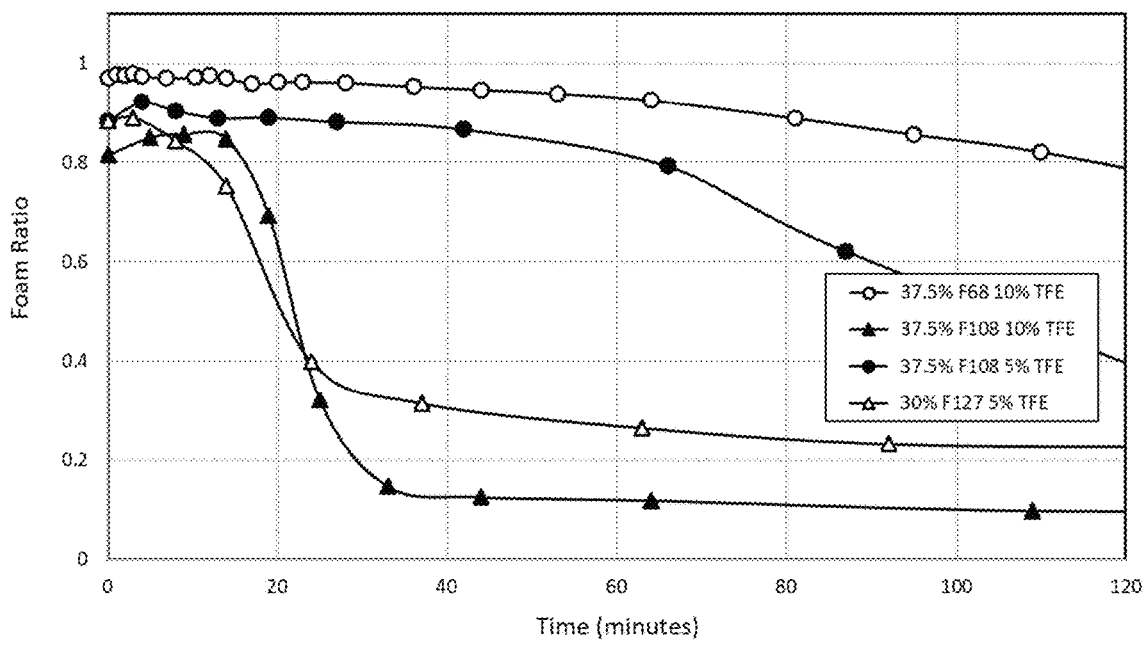
FIG. 13 is a Comparison of Pluronic F68, F108, and F127 foaming polymer formulations.
Figure 13:
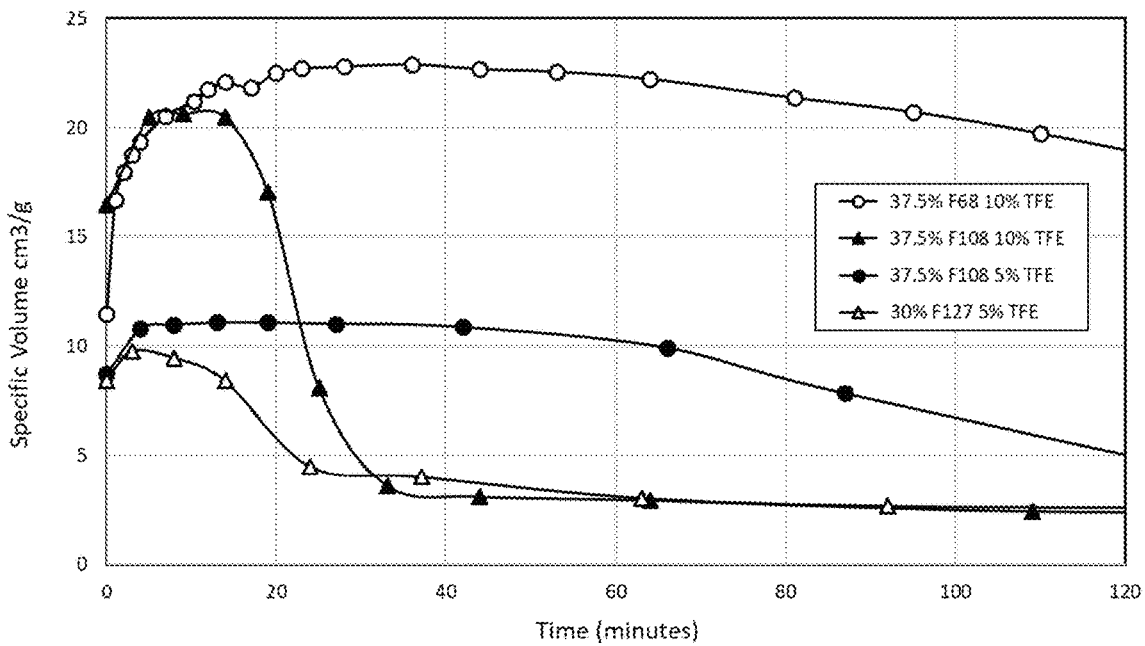

Selected results for the three different Pluronics are compared in FIG. 13. Pluronic F68 formulations consistently produced a uniform and stable foam which captured and retained most of the expanding gas without significant collapse for at least two hours; these results were observed over a range of Pluronic F68 concentrations and a 2-fold difference in TFE content. Pluronic F108 formulations behaved in a similar manner to Pluronic F68, but with one notable difference: although the foam produced using 10% TFE as the expanding gas initially reached approximately the same SV, it collapsed more quickly for F108 than F68 (30 minutes vs. >2 hours). Foams produced using Pluronic F127 also collapsed within 30 minutes; these foams also had a lower peak SV than was achieved with F68 or F108.

Overall it was found that aqueous solutions of each type of Pluronic tested will produce a foam when blended with TFE, but the foams exhibited different characteristics in terms of volume and rate of collapse. The results suggest that the foam properties could be tailored to a specific application, for example if a foam with a longer or shorter lifetime were desired, by selecting the most suitable Pluronic type.

Example 3: In Vivo Evaluation of Foaming Poloxamer Formulation for Hemostasis

Based upon the findings in the foregoing examples, a foaming Pluronic F68-based formulation was selected for evaluation as a potential interventional treatment in a porcine model of acute traumatic non-compressible abdominal hemorrhage.

These following studies were performed using the laparoscopic swine model of non-compressible torso hemorrhage (NCTH) developed by Dr James Ross, as described in "A Laparoscopic Swine Model of Non-Compressible Torso Hemorrhage" James D. Ross Ph D, et al. J Trauma Acute Care Surg, Volume 77, Number 3, Supplement 2, which is hereby incorporated by reference. The laparoscopic approach maintains both the integrity of the peritoneum and the natural tamponade effect of an intact abdominal wall while preserving the intrinsic physiologic responses to hemorrhage and therefore provides a model of NCTH that reflects clinically relevant physiology in trauma and uncontrolled hemorrhage. For splenectomized animals without intervention, the mortality rate in this model was 67%.

Preparation of Foaming Pluronic F68 Formulation: Since a larger volume was required for the in vivo studies, a larger delivery container was used that was functionally equivalent to that shown in FIG. 3. The delivery container was filled with a 45% w/w aqueous Pluronic F68 solution, followed by 10% w/w of TFE, essentially as described in Example 1. However, mechanical stirring was not used to mix the Pluronic F68 solution with the TFE. Instead, after the TFE was added to the container, the pressure in the lower space was reduced to below the vapor pressure of the TFE to create a headspace, and the contents were then mixed by manually shaking the container. After approximately one minute of shaking, the contents increased in viscosity indicating that the components had combined together. Since the delivery containers used for these studies did not have clear walls, the contents could not be observed directly. Therefore, in preliminary tests to evaluate the effectiveness of the mixing technique, containers were discharged fully, and the flow rate and appearance of the foam were observed. Surprisingly, it was found that the brief period of manual shaking was adequate to thoroughly mix the two components: throughout the entire discharge period, the appearance of the foam remained identical to visual inspection, including the consistency of bubble size. There was no hesitation in the flow rate or voids in the foam stream to suggest that any TFE remained in unmixed form. This was a very surprising result, which indicated that the two components had remarkable and unexpected miscibility. The fact that such thorough mixing could be achieved without the need for significant mechanical work suggests that the energy state of the blend may be lower than the individual components and therefore that the blend would be likely to exhibit long-term stability.

Experimental Design: The foaming Pluronic F68 formulation was evaluated in six anesthetized adult male Yorkshire swine. All animals were splenectomized prior to the study, and a pressure sensor was placed laparoscopically into the abdomen to allow monitoring the intra-abdominal pressure (IAP). At the start of the experiment (T=0) a Grade V liver injury was created in each animal by laparoscopically transecting a lobe of the liver. To simulate a typical "pre-hospital" care scenario, the injured liver was allowed to bleed for 10 minutes prior to intervention. At T=10, the foaming Pluronic F68 formulation was delivered to the abdominal cavity via a laparoscopic trocar until the TAP reached 60 mmHg, which was achieved in approximately 1-2 minutes. The delivery was then halted, and the pressure was monitored. Additional foaming Pluronic F68 formulation was delivered as necessary to maintain the TAP approximately 60 mmHg for a minimum of 5 minutes. To avoid ischemic damage to the abdominal organs, the TAP was then allowed to naturally collapse over time. The experiment was terminated one hour after injury (T=60) after which the animals were euthanized, and necropsy performed.

Figure 14:
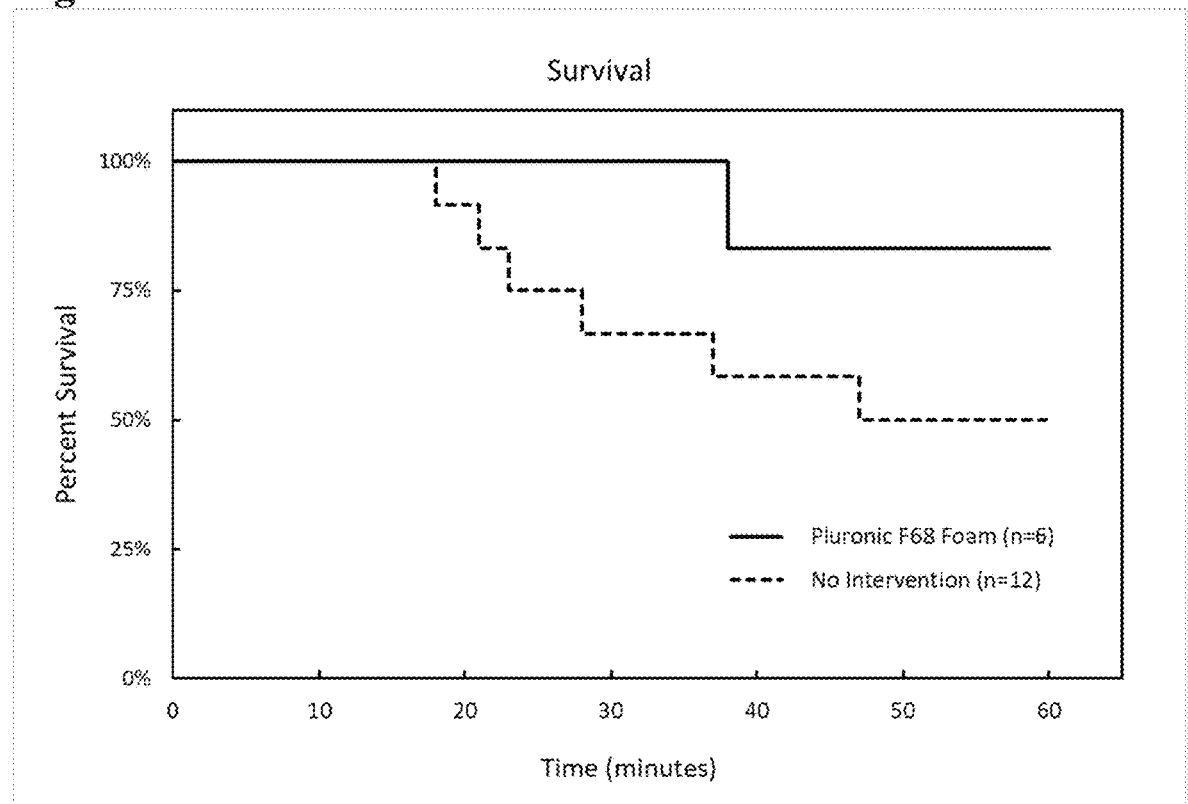
FIG. 14 is a graph of porcine survival over 60 minutes after injury with intraperitoneal deployment of Pluronic F68 foam held at a pressure of 60 mmHg for at least 5 minutes.

Results: FIG. 14 compares the survival of the group of six animals that received the foaming Pluronic F68 formulation against a historic group of twelve animals that received no intervention. Five of the six animals in the intervention group (83%) survived for 60 minutes after injury compared to six of twelve (50%) in the historic control group. The one animal in the intervention group that did not survive had noticeably poor vital signs at T=10, prior to intervention. The results suggest the foaming Pluronic F68 formulation prolonged survival in the intervention group, although the number of animals did not allow for a statistical comparison.

At necropsy, the foaming Pluronic F68 formulation was found to have formed a thick viscous translucent gel in contact with the intra-abdominal organs. The gel did not interfere with the visibility of, or access to, the damaged organ and was easily removed by hand or by irrigation with cold liquid.

CONCLUSIONS

Non-foaming reverse phase Pluronic solutions have been successfully employed and commercialized for control or prevention of bleeding from small blood vessels during surgical procedures, and their wider use has also been proposed for the emergency management of other types of hemorrhage, such as bleeding from deep wounds or within a body cavity, which can be difficult to control by other means such as direct compression. However, all reverse phase solutions have certain inherent characteristics which have hitherto limited their suitability for emergency use and/or for control of severe hemorrhage:

1. It is necessary for the solution to be in the liquid phase prior to delivery to the patient. Consequently, it is necessary to either store the Pluronic solution at a low temperature (i.e., below its gelation temperature) until it is required, or alternatively to provide an external means to cool the solution immediately before use. The need for the solution to be either refrigerated or cooled by some other means before use is particularly undesirable for emergency treatment of hemorrhage in the pre-hospital environment.
2. Control of bleeding from small blood vessels requires only a relatively small volume of reverse phase Pluronic solution (e.g. less than 1 mL). However, a much larger volume is required for control of hemorrhage from a large wound or within a body cavity. To attempt to control intra-abdominal hemorrhage using a simple non-foaming Pluronic solution, it would be necessary to introduce several liters of chilled liquid abdomen. The solution, which consists predominantly of water, has a very high specific heat capacity. Therefore, a significant amount of heat would be required to warm the solution until it reaches the gelation temperature, which raises several potential problems:

a) Gelation may occur only slowly or not at all.
b) Depending upon the rate of heat transfer from the body tissues, the temperature of the polymer solution may increase only very slowly, and it may take an unacceptably long time to become a gel. For a large volume of polymer solution, the total amount of heat that can be drawn from the tissues may be insufficient achieve the gelation temperature. Particularly in the case of the abdomen, the amount of heat available is relatively limited since much of the abdomen is bounded by the abdominal wall, which is relatively thin and not highly vascularized.
c) There is a risk of inducing hypothermia, which could not only have significant adverse systemic consequences, but may also compromise the control of hemorrhage by reducing the ability of the blood to clot.

These deficiencies are addressed by the delivery of the Pluronic solution as a foam rather than as bulk liquid. The foaming formulations described herein rely upon the internal, intrinsic cooling effect of the expanding gas to reduce the temperature of the polymer solution at the instant it is dispensed. Therefore, it is not necessary to pre-chill the delivery container or to provide any external means of cooling. This is an important distinction from the prior art relating to Pluronic solutions which requires the container to be cooled before use in order to convert the polymer solution to a low viscosity liquid.

The foaming formulations described herein also require a much smaller amount of the Pluronic solution to completely fill the wound or body cavity than would be needed for a non-foaming solution. As shown in the examples, a suitable foaming polymer solution can expand at least 25-fold after it is dispensed. Consequently, the total heat capacity of the foam will be much lower than an equivalent final volume of a non-foaming solution, and therefore the amount of heat absorbed by the foamed polymer solution will also be proportionately lower. Note also that the foam has a thermal insulating effect because it greatly reduces mixing due to convection, which would otherwise occur if the solution was in liquid form. The insulating effect will tend to retain the heat in the layer of foam in contact with, or in close proximity to, the internal surfaces of the cavity, thereby promoting gelation precisely where it is required, while slowing the rate of heat transfer to the bulk of the polymer solution.

Examples have been presented herein which demonstrate the features and advantages of certain synthetic polymer formulations representing embodiments of the invention. These examples are not intended to limit the scope of the invention to any specific formulations of synthetic polymers, gases, or volatile liquids and/or concentrations or combinations thereof. It will be apparent to those skilled in the art that formulations containing other poloxamers, other synthetic polymers, other expanding gases, and optionally other components including compounds intended to build and stabilize the foam may also be used. It will also be apparent that agents to assist in the control of hemorrhage or to provide other therapeutic benefits may also be advantageously included within and delivered by the synthetic polymer formulation.

There have also been illustrated and described herein certain systems and methods for delivering said synthetic polymer formulations to the body. While particular embodiments have been described, it is not intended that the invention be limited thereto, as it is intended that the invention be as broad in scope as the art will allow and that the specification be read likewise.

Furthermore, while parts of the embodiments of the invention were described as having certain shapes, and being made of certain materials, it will be appreciated that other materials and shapes can be utilized. For example, it is evident that the system could easily be modified to deliver other therapeutic and/or diagnostic liquids, gases, solutions, and/or suspensions to the body. For another example, it is evident that the synthetic polymer formulation could be used to stop bleeding in the abdominal cavity, thoracic cavity, junctionally, externally, intravaginally, intrauterine, intracranially, intranasally, and/or into puncture or other wounds (e.g. abscess). For areas that are not naturally a contained space or could have easy spillage from within it (e.g. nares, uterus after delivery), the system may also contain a means for blocking exit of the foam from part of the cavity (e.g. an inflatable balloon, packing) to allow for use. It is also evident that the synthetic polymer formulation could be inserted into a cavity via other means (e.g. simple tubing, naked needle, Veress needle, open surgical approach, direct spray) and that the synthetic polymer formulation could be used without the delivery device or the delivery device could be used to deliver other materials. It will therefore be appreciated by those skilled in the art that yet other modifications could be made to the provided invention without deviating from its spirit and scope as so claimed.

The following references include information relevant to the devices and methods of the present invention and are hereby incorporated by reference: Eastridge et al. Death on the battlefield (2001-2011): Implications for the future of combat casualty care. J Trauma Acute Care Surg. 73(6) Sup 5.; and Clarke, J R et al. Time to Laparotomy for Intra-abdominal Bleeding from Trauma Does Affect Survival for Delays Up to 90 Minutes. Journal of Trauma-Injury Infection & Critical Care. 2002 52(3): p 420-425.

The invention claimed is:

1. A pressurized therapeutic composition configured to be stored in a valved container designed to maintain the composition under pressure and dispense the composition upon opening the valve thereof, the composition comprising:
   an aqueous solution of a copolymer of ethylene oxide and propylene oxide over about 5% w/w, wherein the copolymer solution undergoes a reverse phase change from a liquid to a gel upon warming;
   a liquefied hydrofluorocarbon gas comprising at least 2.5% of a total mass of the composition, wherein the liquefied gas and the aqueous solution are blended together to form a stable and macroscopically homogeneous solution; and
   wherein the liquefied gas evaporates to cause the aqueous solution to foam after the composition is dispensed from the container; wherein an apparatus is configured to be attached to the pressurized valved container to deliver the therapeutic composition to an external wound or area.

2. The pressurized therapeutic composition of claim 1, wherein the copolymer of ethylene oxide and propylene oxide is a poloxamer selected from the group consisting of: P188, P237, P338 and P407.

3. The pressurized therapeutic composition of claim 1 wherein, the copolymer of ethylene oxide and propylene oxide is poloxamer P188; and
   the concentration of poloxamer in the aqueous solution is between about 40% and about 50% w/w.

4. The pressurized therapeutic composition of claim 1, wherein the hydrofluorocarbon is 1,1,1,2-Tetrafluoroethane or a blend of 1,1,1,2-Tetrafluoroethane with other hydrofluorocarbons.

5. The pressurized therapeutic composition of claim 1, wherein the copolymer of ethylene oxide and propylene oxide is poloxamer P407; and the concentration of the poloxamer in the aqueous solution is between about 20% and about 40% w/w.

6. The pressurized therapeutic composition of claim 1, wherein the composition is sterile.

7. The pressurized therapeutic composition of claim 1, wherein the pressurized therapeutic composition further comprises one or more active therapeutic agents.

8. The pressurized therapeutic composition of claim 7, wherein the one or more active therapeutic agents includes a procoagulant agent.

9. The pressurized therapeutic composition of claim 8, wherein the one or more active therapeutic agents includes an antibacterial agent.

10. The pressurized therapeutic composition of claim 1, where the apparatus is configured to deliver the therapeutic composition via spraying.

11. The pressurized therapeutic composition of claim 1, wherein the copolymer of ethylene oxide and propylene oxide is a mixture of more than one poloxamer.

12. The pressurized therapeutic composition of claim 1, wherein the reverse phase change occurs when warming approximately to external body temperature.

13. The pressurized therapeutic composition of claim 1, wherein the reverse phase change occurs when warming approximately to internal body temperature.

14. The pressurized therapeutic composition of claim 1, wherein the aqueous solution of a copolymer of ethylene oxide and propylene oxide is between about 20% and 50% w/w.

15. A pressurized therapeutic composition configured to be stored in a valved container designed to maintain the composition under pressure and dispense the composition upon opening the valve thereof, the composition comprising:
an aqueous solution of a copolymer of ethylene oxide and propylene oxide between about 20% and 50% w/w;
a liquefied hydrofluorocarbon gas comprising at least 2.5% of a total mass of the composition, wherein the liquefied gas and the aqueous solution are blended together to form a stable and macroscopically homogeneous solution; and
wherein the liquefied gas evaporates to cause the aqueous solution to foam after the composition is dispensed from the container; wherein an apparatus is configured to be attached to the pressurized valved container to deliver the therapeutic composition to an external wound or area.

16. The pressurized therapeutic composition of claim 15, wherein the copolymer solution undergoes a reverse phase change from a liquid to a gel upon warming.

17. The pressurized therapeutic composition of claim 15, wherein the pressurized therapeutic composition further comprises one or more active therapeutic agents.

18. The pressurized therapeutic composition of claim 17, wherein the one or more active therapeutic agents includes a procoagulant agent.

19. The pressurized therapeutic composition of claim 17, wherein the one or more active therapeutic agents includes an antibacterial agent.

\* \* \* \* \*